United States Patent
Baker, Jr.

(10) Patent No.: US 8,577,436 B2
(45) Date of Patent: *Nov. 5, 2013

(54) MEDICAL SENSOR FOR REDUCING SIGNAL ARTIFACTS AND TECHNIQUE FOR USING THE SAME

(75) Inventor: Clark R. Baker, Jr., Newman, CA (US)

(73) Assignee: Covidien LP, Mansfield, MA (US)

( * ) Notice: Subject to any disclaimer, the term of this patent is extended or adjusted under 35 U.S.C. 154(b) by 53 days.

This patent is subject to a terminal disclaimer.

(21) Appl. No.: 13/412,421

(22) Filed: Mar. 5, 2012

(65) Prior Publication Data

US 2012/0165632 A1    Jun. 28, 2012

Related U.S. Application Data

(63) Continuation of application No. 11/507,814, filed on Aug. 22, 2006, now Pat. No. 8,145,288.

(51) Int. Cl.
*A61B 5/1455* (2006.01)

(52) U.S. Cl.
USPC ............................ 600/344; 600/310; 600/323

(58) Field of Classification Search
USPC ......... 600/310, 322, 323, 324, 335, 340, 344, 600/473, 476; 356/41
See application file for complete search history.

(56) References Cited

U.S. PATENT DOCUMENTS

| | | |
|---|---|---|
| 3,403,555 A | 10/1968 | Versaci et al. |
| 3,536,545 A | 10/1970 | Traynor et al. |
| D222,454 S | 10/1971 | Beeber |
| 3,721,813 A | 3/1973 | Condon et al. |
| 4,098,772 A | 7/1978 | Bonk et al. |
| D250,275 S | 11/1978 | Bond |
| D251,387 S | 3/1979 | Ramsey et al. |
| D262,488 S | 12/1981 | Rossman et al. |
| 4,321,930 A | 3/1982 | Jobsis et al. |
| 4,334,544 A | 6/1982 | Hill et al. |
| 4,350,165 A | 9/1982 | Striese |
| 4,353,372 A | 10/1982 | Ayer |
| 4,380,240 A | 4/1983 | Jobsis et al. |
| 4,406,289 A | 9/1983 | Wesseling et al. |
| 4,510,551 A | 4/1985 | Brainard, II |
| 4,510,938 A | 4/1985 | Jobsis et al. |
| 4,586,513 A | 5/1986 | Hamaguri |

(Continued)

FOREIGN PATENT DOCUMENTS

| | | |
|---|---|---|
| CN | 11080192 | 11/2007 |
| DE | 3405444 | 8/1985 |

(Continued)

OTHER PUBLICATIONS

Rheineck-Leyssius et al. "Advanced Pulse Oximeter Signal Processing Technology Compared to Simple Averaging: I. Effect on Frequency of Alarms in the Operating Room" *Journal of clinical Anestesia* vol. 11 pp. 192-195 (1990).

(Continued)

*Primary Examiner* — Eric Winakur
*Assistant Examiner* — Chu Chuan (JJ) Liu
(74) *Attorney, Agent, or Firm* — Fletcher Yoder PC

(57) ABSTRACT

A sensor may be adapted to reduce signal artifacts by deflecting the effects of outside forces and sensor motion. A sensor is provided with a rigid annular structure adapted to reduce the effect of motion of a sensor emitter and/or detector. Further, a method of deflecting or minimizing outside forces and sensor motion is also provided.

20 Claims, 6 Drawing Sheets

(56) References Cited

U.S. PATENT DOCUMENTS

| | | |
|---|---|---|
| 4,603,700 A | 8/1986 | Nichols et al. |
| 4,621,643 A | 11/1986 | New, Jr. et al. |
| 4,653,498 A | 3/1987 | New, Jr. et al. |
| 4,677,528 A | 6/1987 | Miniet |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,719,924 A | 1/1988 | Crittenden et al. |
| 4,722,120 A | 2/1988 | Lu |
| 4,726,382 A | 2/1988 | Boehmer et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,783,815 A | 11/1988 | Buttner |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hansmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,041,187 A | 8/1991 | Hink et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,086,229 A | 2/1992 | Rosenthal et al. |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| D326,715 S | 6/1992 | Schmidt |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,167,230 A | 12/1992 | Chance |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,207 A | 6/1993 | Rosenthal |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,267,566 A | 12/1993 | Choucair et al. |
| 5,273,036 A | 12/1993 | Kronberg et al. |
| 5,275,159 A | 1/1994 | Griebel |
| 5,278,627 A | 1/1994 | Aoyagi et al. |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Freidman et al. |
| 5,311,865 A | 5/1994 | Mayeux |
| 5,313,940 A | 5/1994 | Fuse et al. |
| 5,323,776 A | 6/1994 | Blakely et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,348,005 A | 9/1994 | Merrick et al. |
| 5,349,519 A | 9/1994 | Kaestle |

(56) References Cited

U.S. PATENT DOCUMENTS

| | | | |
|---|---|---|---|
| 5,349,952 | A | 9/1994 | McCarthy et al. |
| 5,349,953 | A | 9/1994 | McCarthy et al. |
| 5,351,685 | A | 10/1994 | Potratz |
| 5,353,799 | A | 10/1994 | Chance |
| 5,355,880 | A | 10/1994 | Thomas et al. |
| 5,355,882 | A | 10/1994 | Ukawa et al. |
| 5,361,758 | A | 11/1994 | Hall et al. |
| 5,365,066 | A | 11/1994 | Krueger, Jr. et al. |
| 5,368,025 | A | 11/1994 | Young et al. |
| 5,368,026 | A | 11/1994 | Swedlow et al. |
| 5,368,224 | A | 11/1994 | Richardson et al. |
| 5,372,136 | A | 12/1994 | Steuer et al. |
| 5,377,675 | A | 1/1995 | Ruskewicz et al. |
| 5,385,143 | A | 1/1995 | Aoyagi |
| 5,387,122 | A | 2/1995 | Goldberger et al. |
| 5,390,670 | A | 2/1995 | Centa et al. |
| 5,392,777 | A | 2/1995 | Swedlow et al. |
| 5,398,680 | A | 3/1995 | Polson et al. |
| 5,402,777 | A | 4/1995 | Warring et al. |
| 5,402,779 | A | 4/1995 | Chen et al. |
| 5,411,023 | A | 5/1995 | Morris, Sr. et al. |
| 5,411,024 | A | 5/1995 | Thomas et al. |
| 5,413,099 | A | 5/1995 | Schmidt et al. |
| 5,413,100 | A | 5/1995 | Barthelemy et al. |
| 5,413,101 | A | 5/1995 | Sugiura |
| 5,413,102 | A | 5/1995 | Schmidt et al. |
| 5,417,207 | A | 5/1995 | Young et al. |
| 5,421,329 | A | 6/1995 | Casciani et al. |
| 5,425,360 | A | 6/1995 | Nelson |
| 5,425,362 | A | 6/1995 | Siker et al. |
| 5,427,093 | A | 6/1995 | Ogawa et al. |
| 5,429,128 | A | 7/1995 | Cadell et al. |
| 5,429,129 | A | 7/1995 | Lovejoy et al. |
| 5,431,159 | A | 7/1995 | Baker et al. |
| 5,431,170 | A | 7/1995 | Mathews |
| 5,437,275 | A | 8/1995 | Amundsen et al. |
| 5,438,986 | A | 8/1995 | Disch et al. |
| 5,448,991 | A | 9/1995 | Polson et al. |
| 5,452,717 | A | 9/1995 | Branigan et al. |
| 5,465,714 | A | 11/1995 | Scheuing |
| 5,469,845 | A | 11/1995 | DeLonzor et al. |
| RE35,122 | E | 12/1995 | Corenman et al. |
| 5,482,034 | A | 1/1996 | Lewis et al. |
| 5,482,036 | A | 1/1996 | Diab et al. |
| 5,485,847 | A | 1/1996 | Baker, Jr. |
| 5,490,505 | A | 2/1996 | Diab et al. |
| 5,490,523 | A | 2/1996 | Isaacson et al. |
| 5,491,299 | A | 2/1996 | Naylor et al. |
| 5,494,032 | A | 2/1996 | Robinson et al. |
| 5,494,043 | A | 2/1996 | O'Sullivan et al. |
| 5,497,771 | A | 3/1996 | Rosenheimer |
| 5,499,627 | A | 3/1996 | Steuer et al. |
| 5,503,148 | A | 4/1996 | Pologe et al. |
| 5,505,199 | A | 4/1996 | Kim |
| 5,507,286 | A | 4/1996 | Solenberger |
| 5,511,546 | A | 4/1996 | Hon |
| 5,517,988 | A | 5/1996 | Gerhard |
| 5,520,177 | A | 5/1996 | Ogawa et al. |
| 5,521,851 | A | 5/1996 | Wei et al. |
| 5,522,388 | A | 6/1996 | Ishikawa et al. |
| 5,524,617 | A | 6/1996 | Mannheimer |
| 5,529,064 | A | 6/1996 | Rall et al. |
| 5,533,507 | A | 7/1996 | Potratz et al. |
| 5,551,423 | A | 9/1996 | Sugiura |
| 5,551,424 | A | 9/1996 | Morrison et al. |
| 5,553,614 | A | 9/1996 | Chance |
| 5,553,615 | A | 9/1996 | Carim et al. |
| 5,555,882 | A | 9/1996 | Richardson et al. |
| 5,558,096 | A | 9/1996 | Palatnik |
| 5,560,355 | A | 10/1996 | Merchant et al. |
| 5,564,417 | A | 10/1996 | Chance |
| 5,575,284 | A | 11/1996 | Athan et al. |
| 5,575,285 | A | 11/1996 | Takanashi et al. |
| 5,577,500 | A | 11/1996 | Potratz |
| 5,582,169 | A | 12/1996 | Oda et al. |
| 5,584,296 | A | 12/1996 | Cui et al. |
| 5,588,425 | A | 12/1996 | Sackner et al. |
| 5,588,427 | A | 12/1996 | Tien |
| 5,590,652 | A | 1/1997 | Inai |
| 5,595,176 | A | 1/1997 | Yamaura |
| 5,596,986 | A | 1/1997 | Goldfarb |
| 5,611,337 | A | 3/1997 | Bukta |
| 5,617,852 | A | 4/1997 | MacGregor |
| 5,619,992 | A | 4/1997 | Guthrie et al. |
| 5,626,140 | A | 5/1997 | Feldman et al. |
| 5,629,992 | A | 5/1997 | Amersfoort et al. |
| 5,630,413 | A | 5/1997 | Thomas et al. |
| 5,632,272 | A | 5/1997 | Diab et al. |
| 5,632,273 | A | 5/1997 | Suzuki |
| 5,634,459 | A | 6/1997 | Gardosi |
| 5,638,593 | A | 6/1997 | Gerhardt et al. |
| 5,638,816 | A | 6/1997 | Kiani-Azarbayjany et al. |
| 5,638,818 | A | 6/1997 | Diab et al. |
| 5,645,060 | A | 7/1997 | Yorkey et al. |
| 5,645,440 | A | 7/1997 | Tobler et al. |
| 5,660,567 | A | 8/1997 | Nierlich et al. |
| 5,662,105 | A | 9/1997 | Tien |
| 5,662,106 | A | 9/1997 | Swedlow et al. |
| 5,664,270 | A | 9/1997 | Bell et al. |
| 5,666,952 | A | 9/1997 | Fuse et al. |
| 5,671,529 | A | 9/1997 | Nelson |
| 5,673,692 | A | 10/1997 | Schulze et al. |
| 5,673,693 | A | 10/1997 | Solenberger |
| 5,676,139 | A | 10/1997 | Goldberger et al. |
| 5,676,141 | A | 10/1997 | Hollub |
| 5,678,544 | A | 10/1997 | DeLonzor et al. |
| 5,680,857 | A | 10/1997 | Pelikan et al. |
| 5,685,299 | A | 11/1997 | Diab et al. |
| 5,685,301 | A | 11/1997 | Klomhaus |
| 5,687,719 | A | 11/1997 | Sato et al. |
| 5,687,722 | A | 11/1997 | Tien et al. |
| 5,692,503 | A | 12/1997 | Kuenstner |
| 5,692,505 | A | 12/1997 | Fouts |
| 5,709,205 | A | 1/1998 | Bukta |
| 5,713,355 | A | 2/1998 | Richardson et al. |
| 5,724,967 | A | 3/1998 | Venkatachalam |
| 5,727,547 | A | 3/1998 | Levinson et al. |
| 5,730,124 | A | 3/1998 | Yamauchi |
| 5,731,582 | A | 3/1998 | West |
| D393,830 | S | 4/1998 | Tobler et al. |
| 5,743,260 | A | 4/1998 | Chung et al. |
| 5,743,262 | A | 4/1998 | Lepper, Jr. et al. |
| 5,743,263 | A | 4/1998 | Baker, Jr. |
| 5,746,206 | A | 5/1998 | Mannheimer |
| 5,746,697 | A | 5/1998 | Swedlow et al. |
| 5,752,914 | A | 5/1998 | DeLonzor et al. |
| 5,755,226 | A | 5/1998 | Carim et al. |
| 5,758,644 | A | 6/1998 | Diab et al. |
| 5,760,910 | A | 6/1998 | Lepper, Jr. et al. |
| 5,766,125 | A | 6/1998 | Aoyagi et al. |
| 5,766,127 | A | 6/1998 | Pologe et al. |
| 5,769,785 | A | 6/1998 | Diab et al. |
| 5,772,587 | A | 6/1998 | Gratton et al. |
| 5,774,213 | A | 6/1998 | Trebino et al. |
| 5,776,058 | A | 7/1998 | Levinson et al. |
| 5,776,059 | A | 7/1998 | Kaestle |
| 5,779,630 | A | 7/1998 | Fein et al. |
| 5,779,631 | A | 7/1998 | Chance |
| 5,782,237 | A | 7/1998 | Casciani et al. |
| 5,782,756 | A | 7/1998 | Mannheimer |
| 5,782,757 | A | 7/1998 | Diab et al. |
| 5,782,758 | A | 7/1998 | Ausec et al. |
| 5,786,592 | A | 7/1998 | Hök |
| 5,788,634 | A | 8/1998 | Suda et al. |
| 5,790,729 | A | 8/1998 | Pologe et al. |
| 5,792,052 | A | 8/1998 | Isaacson et al. |
| 5,795,292 | A | 8/1998 | Lewis et al. |
| 5,797,841 | A | 8/1998 | DeLonzor et al. |
| 5,800,348 | A | 9/1998 | Kaestle |
| 5,800,349 | A | 9/1998 | Isaacson et al. |
| 5,803,910 | A | 9/1998 | Potratz |
| 5,807,246 | A | 9/1998 | Sakaguchi et al. |
| 5,807,247 | A | 9/1998 | Merchant et al. |
| 5,807,248 | A | 9/1998 | Mills |

(56) References Cited

U.S. PATENT DOCUMENTS

| | | |
|---|---|---|
| 5,810,723 A | 9/1998 | Aldrich |
| 5,810,724 A | 9/1998 | Gronvall |
| 5,813,980 A | 9/1998 | Levinson et al. |
| 5,817,008 A | 10/1998 | Rafert et al. |
| 5,817,009 A | 10/1998 | Rosenheimer et al. |
| 5,817,010 A | 10/1998 | Hibl |
| 5,818,985 A | 10/1998 | Merchant et al. |
| 5,820,550 A | 10/1998 | Polson et al. |
| 5,823,950 A | 10/1998 | Diab et al. |
| 5,823,952 A | 10/1998 | Levinson et al. |
| 5,827,179 A | 10/1998 | Lichter et al. |
| 5,827,182 A | 10/1998 | Raley et al. |
| 5,829,439 A | 11/1998 | Yokosawa et al. |
| 5,830,135 A | 11/1998 | Bosque et al. |
| 5,830,136 A | 11/1998 | DeLonzor et al. |
| 5,830,137 A | 11/1998 | Scharf |
| 5,839,439 A | 11/1998 | Nierlich et al. |
| RE36,000 E | 12/1998 | Swedlow et al. |
| 5,842,979 A | 12/1998 | Jarman et al. |
| 5,842,981 A | 12/1998 | Larsen et al. |
| 5,842,982 A | 12/1998 | Mannheimer |
| 5,846,190 A | 12/1998 | Woehrle |
| 5,851,178 A | 12/1998 | Aronow |
| 5,851,179 A | 12/1998 | Ritson et al. |
| 5,853,364 A | 12/1998 | Baker, Jr. et al. |
| 5,860,919 A | 1/1999 | Kiani/Azarbayjany et al. |
| 5,865,736 A | 2/1999 | Baker, Jr. et al. |
| 5,879,294 A | 3/1999 | Anderson et al. |
| 5,885,213 A | 3/1999 | Richardson et al. |
| 5,890,929 A | 4/1999 | Mills et al. |
| 5,891,021 A | 4/1999 | Dillon et al. |
| 5,891,022 A | 4/1999 | Pologe |
| 5,891,024 A | 4/1999 | Jarman et al. |
| 5,891,025 A | 4/1999 | Buschmann et al. |
| 5,891,026 A | 4/1999 | Wang et al. |
| 5,902,235 A | 5/1999 | Lewis et al. |
| 5,910,108 A | 6/1999 | Solenberger |
| 5,911,690 A | 6/1999 | Rall |
| 5,912,656 A | 6/1999 | Tham et al. |
| 5,913,819 A | 6/1999 | Taylor et al. |
| 5,916,154 A | 6/1999 | Hobbs et al. |
| 5,916,155 A | 6/1999 | Levinson et al. |
| 5,919,133 A | 7/1999 | Taylor et al. |
| 5,919,134 A | 7/1999 | Diab |
| 5,920,263 A | 7/1999 | Huttenhoff et al. |
| 5,921,921 A | 7/1999 | Potratz et al. |
| 5,922,607 A | 7/1999 | Bernreuter |
| 5,924,979 A | 7/1999 | Swedlow et al. |
| 5,924,980 A | 7/1999 | Coetzee |
| 5,924,982 A | 7/1999 | Chin |
| 5,924,985 A | 7/1999 | Jones |
| 5,934,277 A | 8/1999 | Mortz |
| 5,934,925 A | 8/1999 | Tobler et al. |
| 5,940,182 A | 8/1999 | Lepper, Jr. et al. |
| 5,954,644 A | 9/1999 | Dettling et al. |
| 5,957,840 A | 9/1999 | Terasawa et al. |
| 5,960,610 A | 10/1999 | Levinson et al. |
| 5,961,450 A | 10/1999 | Merchant et al. |
| 5,961,452 A | 10/1999 | Chung et al. |
| 5,964,701 A | 10/1999 | Asada et al. |
| 5,971,930 A | 10/1999 | Elghazzawi |
| 5,978,691 A | 11/1999 | Mills |
| 5,978,693 A | 11/1999 | Hamilton et al. |
| 5,983,120 A | 11/1999 | Groner et al. |
| 5,983,122 A | 11/1999 | Jarman et al. |
| 5,987,343 A | 11/1999 | Kinast |
| 5,991,648 A | 11/1999 | Levin |
| 5,995,855 A | 11/1999 | Kiani et al. |
| 5,995,856 A | 11/1999 | Mannheimer et al. |
| 5,995,858 A | 11/1999 | Kinast |
| 5,995,859 A | 11/1999 | Takahashi |
| 5,997,343 A | 12/1999 | Mills et al. |
| 5,999,834 A | 12/1999 | Wang et al. |
| 6,002,952 A | 12/1999 | Diab et al. |
| 6,005,658 A | 12/1999 | Kaluza et al. |
| 6,006,120 A | 12/1999 | Levin |
| 6,011,985 A | 1/2000 | Athan et al. |
| 6,011,986 A | 1/2000 | Diab et al. |
| 6,014,576 A | 1/2000 | Raley et al. |
| 6,018,673 A | 1/2000 | Chin et al. |
| 6,018,674 A | 1/2000 | Aronow |
| 6,022,321 A | 2/2000 | Amano et al. |
| 6,023,541 A | 2/2000 | Merchant et al. |
| 6,026,312 A | 2/2000 | Shemwell et al. |
| 6,026,314 A | 2/2000 | Amerov et al. |
| 6,031,603 A | 2/2000 | Fine et al. |
| 6,035,223 A | 3/2000 | Baker, Jr. |
| 6,036,642 A | 3/2000 | Diab et al. |
| 6,041,247 A | 3/2000 | Weckstrom et al. |
| 6,044,283 A | 3/2000 | Fein et al. |
| 6,047,201 A | 4/2000 | Jackson, III |
| 6,055,447 A | 4/2000 | Weil |
| 6,061,584 A | 5/2000 | Lovejoy et al. |
| 6,064,898 A | 5/2000 | Aldrich |
| 6,064,899 A | 5/2000 | Fein et al. |
| 6,067,462 A | 5/2000 | Diab et al. |
| 6,073,038 A | 6/2000 | Wang et al. |
| 6,078,828 A | 6/2000 | Yasuda |
| 6,078,829 A | 6/2000 | Uchida |
| 6,078,833 A | 6/2000 | Hueber |
| 6,081,735 A | 6/2000 | Diab et al. |
| 6,083,157 A | 7/2000 | Noller |
| 6,083,172 A | 7/2000 | Baker, Jr. et al. |
| 6,088,607 A | 7/2000 | Diab et al. |
| 6,094,592 A | 7/2000 | Yorkey et al. |
| 6,095,974 A | 8/2000 | Shemwell et al. |
| 6,104,938 A | 8/2000 | Huiku et al. |
| 6,104,939 A | 8/2000 | Groner |
| 6,112,107 A | 8/2000 | Hannula |
| 6,113,541 A | 9/2000 | Dias et al. |
| 6,115,621 A | 9/2000 | Chin |
| 6,122,535 A | 9/2000 | Kaestle et al. |
| 6,133,994 A | 10/2000 | Mathews et al. |
| 6,135,952 A | 10/2000 | Coetzee |
| 6,144,444 A | 11/2000 | Haworth et al. |
| 6,144,867 A | 11/2000 | Walker et al. |
| 6,144,868 A | 11/2000 | Parker |
| 6,149,481 A | 11/2000 | Wang et al. |
| 6,151,107 A | 11/2000 | Schöllerman et al. |
| 6,151,516 A | 11/2000 | Kiani-Azarbayjani et al. |
| 6,151,518 A | 11/2000 | Hayashi |
| 6,152,754 A | 11/2000 | Gerhardt et al. |
| 6,154,667 A | 11/2000 | Miura et al. |
| 6,157,850 A | 12/2000 | Diab et al. |
| 6,159,147 A | 12/2000 | Lichter et al. |
| 6,163,715 A | 12/2000 | Larsen et al. |
| 6,165,005 A | 12/2000 | Mills et al. |
| 6,173,196 B1 | 1/2001 | Delonzor et al. |
| 6,178,343 B1 | 1/2001 | Bindszus et al. |
| 6,179,159 B1 | 1/2001 | Gurley |
| 6,181,958 B1 | 1/2001 | Steuer et al. |
| 6,181,959 B1 | 1/2001 | Schöllerman et al. |
| 6,184,521 B1 | 2/2001 | Coffin, IV et al. |
| 6,188,470 B1 | 2/2001 | Grace |
| 6,192,260 B1 | 2/2001 | Chance |
| 6,195,575 B1 | 2/2001 | Levinson |
| 6,198,951 B1 | 3/2001 | Kosuda et al. |
| 6,206,830 B1 | 3/2001 | Diab et al. |
| 6,213,952 B1 | 4/2001 | Finarov et al. |
| 6,217,523 B1 | 4/2001 | Amano et al. |
| 6,222,189 B1 | 4/2001 | Misner et al. |
| 6,223,064 B1 | 4/2001 | Lynn |
| 6,226,539 B1 | 5/2001 | Potratz |
| 6,226,540 B1 | 5/2001 | Bernreuter et al. |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |

(56) References Cited

U.S. PATENT DOCUMENTS

| | | |
|---|---|---|
| 6,261,236 B1 | 7/2001 | Grinblatov |
| 6,263,221 B1 | 7/2001 | Chance et al. |
| 6,263,222 B1 | 7/2001 | Diab et al. |
| 6,263,223 B1 | 7/2001 | Shepherd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,342,039 B1 | 1/2002 | Lynn |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| D455,834 S | 4/2002 | Donars et al. |
| 6,370,408 B1 | 4/2002 | Merchant et al. |
| 6,370,409 B1 | 4/2002 | Chung et al. |
| 6,371,921 B1 | 4/2002 | Caro |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenster |
| 6,393,311 B1 | 5/2002 | Edgar, Jr. et al. |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,400,973 B1 | 6/2002 | Winter |
| 6,402,690 B1 | 6/2002 | Rhee et al. |
| 6,403,944 B1 | 6/2002 | MacKenzie et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,396 B1 | 8/2002 | Cook |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,493,568 B1 | 12/2002 | Bell |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker et al. |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,554,788 B1 | 4/2003 | Hunley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,608,562 B1 | 8/2003 | Kimura et al. |
| 6,609,016 B1 | 8/2003 | Lynn |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,632,181 B2 | 10/2003 | Flaherty |
| 6,640,116 B2 | 10/2003 | Diab |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,916 B2 | 11/2003 | Cook |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wassermann |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |

(56) References Cited

U.S. PATENT DOCUMENTS

| | | |
|---|---|---|
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,712,762 B1 | 3/2004 | Lichter |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,962 B1 | 5/2004 | Katarow |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neil et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tscupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckstrom |
| 6,792,300 B1 | 9/2004 | Diab et al. |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,266 B2 | 11/2004 | Varshneya |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,873,865 B2 | 3/2005 | Steuer et al. |
| 6,879,850 B2 | 4/2005 | Kimball |
| 6,882,874 B2 | 4/2005 | Huiku |
| 6,898,452 B2 | 5/2005 | Al-Ali et al. |
| 6,909,912 B2 | 6/2005 | Melker |
| 6,912,413 B2 | 6/2005 | Rantala et al. |
| 6,920,345 B2 | 7/2005 | Al-Ali et al. |
| 6,931,269 B2 | 8/2005 | Terry |
| 6,934,570 B2 | 8/2005 | Kiani et al. |
| 6,941,162 B2 | 9/2005 | Fudge et al. |
| 6,947,781 B2 | 9/2005 | Asada et al. |
| 6,950,687 B2 | 9/2005 | Al-Ali |
| 6,954,664 B2 | 10/2005 | Sweitzer |
| 6,967,652 B1 | 11/2005 | Nubling et al. |
| 6,968,221 B2 | 11/2005 | Rosenthal |
| 6,979,812 B2 | 12/2005 | Al-Ali |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Okita et al. |
| 6,992,772 B2 | 1/2006 | Block |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali |
| 7,027,850 B2 | 4/2006 | Wasserman |
| 7,039,449 B2 | 5/2006 | Al-Ali |
| 7,043,289 B2 | 5/2006 | Fine et al. |
| 7,047,055 B2 | 5/2006 | Boas et al. |
| 7,060,035 B2 | 6/2006 | Wasserman |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul/Hafiz et al. |
| 7,107,088 B2 | 9/2006 | Aceti |
| 7,112,175 B2 | 9/2006 | Gopinathan et al. |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,134,754 B2 | 11/2006 | Kerr et al. |
| 7,139,559 B2 | 11/2006 | Kenagy et al. |
| 7,142,901 B2 | 11/2006 | Kiani et al. |
| 7,161,484 B2 | 1/2007 | Tsoukalis |
| 7,162,288 B2 | 1/2007 | Nordstrom et al. |
| 7,164,938 B2 | 1/2007 | Geddes et al. |
| 7,190,986 B1 | 3/2007 | Hannula et al. |
| 7,190,987 B2 | 3/2007 | Kindekugel et al. |
| 7,198,778 B2 | 4/2007 | Achilefu et al. |
| 7,215,984 B2 | 5/2007 | Diab et al. |
| 7,225,006 B2 | 5/2007 | Al-Ali et al. |
| 7,228,161 B2 | 6/2007 | Chin |
| 7,236,811 B2 | 6/2007 | Schmitt et al. |

(56) References Cited

U.S. PATENT DOCUMENTS

| | | |
|---|---|---|
| 7,245,953 B1 | 7/2007 | Parker |
| 7,248,910 B2 | 7/2007 | Li et al. |
| 7,254,433 B2 | 8/2007 | Diab et al. |
| 7,254,434 B2 | 8/2007 | Schulz et al. |
| 7,255,006 B2 | 8/2007 | Spanke et al. |
| 7,257,438 B2 | 8/2007 | Kinast |
| 7,263,396 B2 | 8/2007 | Chen et al. |
| 7,272,425 B2 | 9/2007 | Al-Ali |
| 7,280,858 B2 | 10/2007 | Al-Ali et al. |
| 7,292,150 B2 | 11/2007 | Shaw |
| 7,295,866 B2 | 11/2007 | Al-Ali |
| 7,297,119 B2 | 11/2007 | Westbrook et al. |
| 7,305,262 B2 | 12/2007 | Brodnick et al. |
| 7,315,753 B2 | 1/2008 | Baker, Jr. et al. |
| 7,341,559 B2 | 3/2008 | Schulz et al. |
| 7,341,560 B2 | 3/2008 | Henderson et al. |
| 7,359,741 B2 | 4/2008 | Sarussi et al. |
| 7,359,742 B2 | 4/2008 | Maser et al. |
| 7,369,886 B2 | 5/2008 | DeLonzor et al. |
| 7,373,188 B2 | 5/2008 | DeLonzor et al. |
| 7,373,189 B2 | 5/2008 | DeLonzor et al. |
| 7,373,190 B2 | 5/2008 | DeLonzor et al. |
| 7,373,191 B2 | 5/2008 | DeLonzor et al. |
| 7,412,272 B2 | 8/2008 | Medina et al. |
| 7,433,726 B2 | 10/2008 | Perkins |
| 7,435,222 B2 | 10/2008 | Gopinathan et al. |
| 2002/0016537 A1 | 2/2002 | Muz et al. |
| 2002/0026109 A1 | 2/2002 | Diab et al. |
| 2002/0028990 A1 | 3/2002 | Sheperd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0072681 A1 | 6/2002 | Schnall |
| 2002/0103423 A1 | 8/2002 | Chin et al. |
| 2002/0116797 A1 | 8/2002 | Modgil et al. |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0173709 A1 | 11/2002 | Fine et al. |
| 2002/0190863 A1 | 12/2002 | Lynn |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0171662 A1 | 9/2003 | O'Connor et al. |
| 2003/0181799 A1 | 9/2003 | Lindekugel et al. |
| 2003/0187337 A1 | 10/2003 | Tarassenko et al. |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2004/0006261 A1 | 1/2004 | Swedlow et al. |
| 2004/0024326 A1 | 2/2004 | Yeo et al. |
| 2004/0039272 A1 | 2/2004 | Abdul/Hafiz et al. |
| 2004/0039273 A1 | 2/2004 | Terry |
| 2004/0054291 A1 | 3/2004 | Schulz et al. |
| 2004/0068164 A1 | 4/2004 | Diab et al. |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0116787 A1 | 6/2004 | Schnall |
| 2004/0117891 A1 | 6/2004 | Hannula et al. |
| 2004/0122302 A1 | 6/2004 | Mason et al. |
| 2004/0133088 A1 | 7/2004 | Al-Ali |
| 2004/0143172 A1 | 7/2004 | Fudge et al. |
| 2004/0147821 A1 | 7/2004 | Al-Ali et al. |
| 2004/0147824 A1 | 7/2004 | Diab et al. |
| 2004/0158134 A1 | 8/2004 | Diab et al. |
| 2004/0162472 A1 | 8/2004 | Berson et al. |
| 2004/0167381 A1 | 8/2004 | Lichter |
| 2004/0186358 A1 | 9/2004 | Chernow et al. |
| 2004/0199063 A1 | 10/2004 | O'Neil et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215085 A1 | 10/2004 | Schnall |
| 2004/0236196 A1 | 11/2004 | Diab et al. |
| 2004/0257557 A1 | 12/2004 | Block |
| 2004/0260161 A1 | 12/2004 | Melker et al. |
| 2005/0004479 A1 | 1/2005 | Townsend et al. |
| 2005/0014999 A1 | 1/2005 | Rahe-Meyer |
| 2005/0017864 A1 | 1/2005 | Tsoukalis |
| 2005/0020887 A1 | 1/2005 | Goldberg |
| 2005/0033131 A1 | 2/2005 | Chen et al. |
| 2005/0043599 A1 | 2/2005 | O'Mara |
| 2005/0043600 A1 | 2/2005 | Diab et al. |
| 2005/0049468 A1 | 3/2005 | Carlson |
| 2005/0049471 A1 | 3/2005 | Aceti et al. |
| 2005/0059869 A1 | 3/2005 | Scharf et al. |
| 2005/0059870 A1 | 3/2005 | Aceti |
| 2005/0070773 A1 | 3/2005 | Chin |
| 2005/0075546 A1 | 4/2005 | Samsoondar |
| 2005/0075549 A1 | 4/2005 | Kondoh et al. |
| 2005/0075550 A1 | 4/2005 | Lindekugel |
| 2005/0085704 A1 | 4/2005 | Schulz |
| 2005/0090720 A1 | 4/2005 | Wu |
| 2005/0119538 A1 | 6/2005 | Jeon et al. |
| 2005/0163412 A1 | 7/2005 | Glebov et al. |
| 2005/0197548 A1 | 9/2005 | Dietiker |
| 2005/0228248 A1 | 10/2005 | Dietiker |
| 2005/0228299 A1 | 10/2005 | Banet |
| 2005/0228300 A1 | 10/2005 | Jaime et al. |
| 2005/0256386 A1 | 11/2005 | Chan |
| 2005/0272986 A1 | 12/2005 | Smith |
| 2005/0277819 A1 | 12/2005 | Kiani et al. |
| 2005/0283082 A1 | 12/2005 | Geddes et al. |
| 2006/0020179 A1 | 1/2006 | Anderson et al. |
| 2006/0020185 A1 | 1/2006 | Al-Ali |
| 2006/0030764 A1 | 2/2006 | Porges |
| 2006/0036136 A1 | 2/2006 | Shaw |
| 2006/0058594 A1 | 3/2006 | Ishizuka et al. |
| 2006/0058690 A1 | 3/2006 | Bartnik |
| 2006/0064024 A1 | 3/2006 | Schnall |
| 2006/0069319 A1 | 3/2006 | Elhag et al. |
| 2006/0074280 A1 | 4/2006 | Martis |
| 2006/0075257 A1 | 4/2006 | Martis et al. |
| 2006/0079794 A1 | 4/2006 | Liu et al. |
| 2006/0084852 A1 | 4/2006 | Mason et al. |
| 2006/0084878 A1 | 4/2006 | Banet |
| 2006/0089547 A1 | 4/2006 | Sarussi |
| 2006/0106294 A1 | 5/2006 | Maser et al. |
| 2006/0122517 A1 | 6/2006 | Banet |
| 2006/0129039 A1 | 6/2006 | Lindner |
| 2006/0149149 A1 | 7/2006 | Schmid |
| 2006/0155198 A1 | 7/2006 | Schmid |
| 2006/0173257 A1 | 8/2006 | Nagai |
| 2006/0200018 A1 | 9/2006 | Al-Ali |
| 2006/0253010 A1 | 11/2006 | Brady et al. |
| 2006/0276700 A1 | 12/2006 | O'Neil et al. |
| 2007/0021659 A1 | 1/2007 | DeLonzor et al. |
| 2007/0021660 A1 | 1/2007 | DeLonzor et al. |
| 2007/0021662 A1 | 1/2007 | DeLonzor et al. |
| 2007/0027376 A1 | 2/2007 | Todokoro et al. |
| 2007/0027378 A1 | 2/2007 | Delonzor et al. |
| 2007/0027379 A1 | 2/2007 | Delonzor et al. |
| 2007/0027380 A1 | 2/2007 | Delonzar et al. |
| 2007/0032707 A1 | 2/2007 | Coakley et al. |
| 2007/0032708 A1 | 2/2007 | Eghbal et al. |
| 2007/0032709 A1 | 2/2007 | Coakley et al. |
| 2007/0032710 A1 | 2/2007 | Raridan et al. |
| 2007/0032711 A1 | 2/2007 | Coakley et al. |
| 2007/0032712 A1 | 2/2007 | Raridan et al. |
| 2007/0032715 A1 | 2/2007 | Eghbal et al. |
| 2007/0032716 A1 | 2/2007 | Raridan et al. |
| 2007/0038050 A1 | 2/2007 | Sarussi |
| 2007/0060808 A1 | 3/2007 | Hoarau |
| 2007/0073117 A1 | 3/2007 | Raridan |
| 2007/0073121 A1 | 3/2007 | Hoarau et al. |
| 2007/0073122 A1 | 3/2007 | Hoarau |
| 2007/0073123 A1 | 3/2007 | Raridan |

(56) References Cited

U.S. PATENT DOCUMENTS

| | | |
|---|---|---|
| 2007/0073125 A1 | 3/2007 | Hoarau et al. |
| 2007/0073126 A1 | 3/2007 | Raridan |
| 2007/0073128 A1 | 3/2007 | Hoarau |
| 2007/0078315 A1 | 4/2007 | Kling et al. |
| 2007/0078316 A1 | 4/2007 | Hoarau |
| 2007/0106132 A1 | 5/2007 | Elhag et al. |
| 2007/0197887 A1 | 8/2007 | Lunak et al. |
| 2007/0219440 A1 | 9/2007 | Hannula et al. |
| 2007/0260129 A1 | 11/2007 | Chin |
| 2007/0260130 A1 | 11/2007 | Chin |
| 2007/0260131 A1 | 11/2007 | Chin |
| 2007/0287898 A1 | 12/2007 | Lee et al. |
| 2007/0299328 A1 | 12/2007 | Chin et al. |
| 2008/0009691 A1 | 1/2008 | Parker et al. |
| 2008/2000786 | 8/2008 | Berndsen |
| 2008/0230363 A1 | 9/2008 | Yang |
| 2008/0262328 A1 | 10/2008 | Adams |

FOREIGN PATENT DOCUMENTS

| | | |
|---|---|---|
| DE | 3516338 | 11/1986 |
| DE | 3703458 | 8/1988 |
| DE | 3938759 | 5/1991 |
| DE | 4210102 | 9/1993 |
| DE | 4423597 | 8/1995 |
| DE | 19632361 | 2/1997 |
| DE | 69123448 | 5/1997 |
| DE | 19703220 | 7/1997 |
| DE | 19640807 | 9/1997 |
| DE | 19647877 | 4/1998 |
| DE | 10030862 | 1/2002 |
| DE | 20318882 | 4/2004 |
| EP | 0127947 | 5/1984 |
| EP | 00194105 | 9/1986 |
| EP | 204459 | 12/1986 |
| EP | 0262779 | 4/1988 |
| EP | 0315040 | 10/1988 |
| EP | 0314331 | 5/1989 |
| EP | 00352923 | 1/1990 |
| EP | 0360977 | 4/1990 |
| EP | 430340 | 6/1991 |
| EP | 0435500 | 7/1991 |
| EP | 0572684 | 5/1992 |
| EP | 00497021 | 8/1992 |
| EP | 0529412 | 8/1992 |
| EP | 0531631 | 9/1992 |
| EP | 0566354 | 4/1993 |
| EP | 0587009 | 8/1993 |
| EP | 00630203 | 9/1993 |
| EP | 00615723 | 9/1994 |
| EP | 00702931 | 3/1996 |
| EP | 724860 | 8/1996 |
| EP | 00793942 | 9/1997 |
| EP | 0864293 | 9/1998 |
| EP | 01006863 | 10/1998 |
| EP | 01006864 | 10/1998 |
| EP | 0875199 | 11/1998 |
| EP | 00998214 | 12/1998 |
| EP | 0898933 | 3/1999 |
| EP | 805647 | 8/2000 |
| EP | 01332713 | 8/2003 |
| EP | 01469773 | 8/2003 |
| EP | 1502529 | 7/2004 |
| EP | 1491135 | 12/2004 |
| EP | 1807001 | 7/2007 |
| EP | 1905356 | 4/2008 |
| FR | 2685865 | 1/1992 |
| GB | 2259545 | 3/1993 |
| JP | 63275325 | 11/1988 |
| JP | 2013450 | 1/1990 |
| JP | 2111343 | 4/1990 |
| JP | 2191434 | 7/1990 |
| JP | 2237544 | 9/1990 |
| JP | 3170866 | 7/1991 |
| JP | 3173536 | 7/1991 |
| JP | 3245042 | 10/1991 |
| JP | 4174648 | 6/1992 |
| JP | 4191642 | 7/1992 |
| JP | 4332536 | 11/1992 |
| JP | 3124073 | 3/1993 |
| JP | 5049624 | 3/1993 |
| JP | 5049625 | 3/1993 |
| JP | 3115374 | 4/1993 |
| JP | 5212016 | 8/1993 |
| JP | 2005200031 | 8/1993 |
| JP | 06014906 | 1/1994 |
| JP | 6016774 | 3/1994 |
| JP | 3116255 | 4/1994 |
| JP | 6029504 | 4/1994 |
| JP | 6098881 | 4/1994 |
| JP | 6154177 | 6/1994 |
| JP | 6269430 | 9/1994 |
| JP | 6285048 | 10/1994 |
| JP | 7001273 | 1/1995 |
| JP | 7124138 | 5/1995 |
| JP | 7136150 | 5/1995 |
| JP | 3116259 | 6/1995 |
| JP | 3116260 | 6/1995 |
| JP | 7155311 | 6/1995 |
| JP | 7155313 | 6/1995 |
| JP | 3238813 | 7/1995 |
| JP | 7171139 | 7/1995 |
| JP | 3134144 | 9/1995 |
| JP | 7236625 | 9/1995 |
| JP | 7246191 | 9/1995 |
| JP | 8256996 | 10/1996 |
| JP | 9192120 | 7/1997 |
| JP | 10216113 | 8/1998 |
| JP | 10216114 | 8/1998 |
| JP | 10216115 | 8/1998 |
| JP | 10337282 | 12/1998 |
| JP | 11019074 | 1/1999 |
| JP | 11155841 | 6/1999 |
| JP | 11188019 | 7/1999 |
| JP | 11244268 | 9/1999 |
| JP | 20107157 | 4/2000 |
| JP | 20237170 | 9/2000 |
| JP | 21245871 | 9/2001 |
| JP | 22224088 | 8/2002 |
| JP | 22282242 | 10/2002 |
| JP | 23153881 | 5/2003 |
| JP | 23153882 | 5/2003 |
| JP | 23169791 | 6/2003 |
| JP | 23194714 | 7/2003 |
| JP | 23210438 | 7/2003 |
| JP | 23275192 | 9/2003 |
| JP | 23339678 | 12/2003 |
| JP | 24008572 | 1/2004 |
| JP | 24089546 | 3/2004 |
| JP | 24113353 | 4/2004 |
| JP | 24135854 | 5/2004 |
| JP | 24148069 | 5/2004 |
| JP | 24148070 | 5/2004 |
| JP | 24159810 | 6/2004 |
| JP | 24166775 | 6/2004 |
| JP | 24194908 | 7/2004 |
| JP | 24202190 | 7/2004 |
| JP | 24248819 | 9/2004 |
| JP | 24248820 | 9/2004 |
| JP | 24261364 | 9/2004 |
| JP | 24290412 | 10/2004 |
| JP | 24290544 | 10/2004 |
| JP | 24290545 | 10/2004 |
| JP | 24329406 | 11/2004 |
| JP | 24329607 | 11/2004 |
| JP | 24329928 | 11/2004 |
| JP | 24337605 | 12/2004 |
| JP | 24344367 | 12/2004 |
| JP | 24351107 | 12/2004 |
| JP | 25034472 | 2/2005 |
| JP | 25052385 | 3/2005 |
| JP | 25110816 | 4/2005 |
| JP | 25111161 | 4/2005 |

(56) References Cited

FOREIGN PATENT DOCUMENTS

| | | |
|---|---|---|
| JP | 25125106 | 5/2005 |
| JP | 25168600 | 6/2005 |
| JP | 26122458 | 5/2006 |
| JP | 26122693 | 5/2006 |
| JP | 26158555 | 6/2006 |
| JP | 26212161 | 8/2006 |
| JP | 3818211 | 9/2006 |
| JP | 27020836 | 2/2007 |
| JP | 4038280 | 1/2008 |
| WO | WO8909566 | 10/1989 |
| WO | WO9001293 | 2/1990 |
| WO | WO9004352 | 5/1990 |
| WO | WO9101678 | 2/1991 |
| WO | WO9111137 | 8/1991 |
| WO | WO9200513 | 1/1992 |
| WO | WO9221281 | 12/1992 |
| WO | WO9309711 | 5/1993 |
| WO | WO9313706 | 7/1993 |
| WO | WO9316629 | 9/1993 |
| WO | WO9403102 | 2/1994 |
| WO | WO9423643 | 10/1994 |
| WO | WO9502358 | 1/1995 |
| WO | WO9512349 | 5/1995 |
| WO | WO9516970 | 6/1995 |
| WO | WO9613208 | 5/1996 |
| WO | WO9616591 | 6/1996 |
| WO | WO9639927 | 12/1996 |
| WO | WO9736536 | 10/1997 |
| WO | WO9736538 | 10/1997 |
| WO | WO9749330 | 12/1997 |
| WO | WO9809566 | 3/1998 |
| WO | WO9817174 | 4/1998 |
| WO | WO9818382 | 5/1998 |
| WO | WO9843071 | 10/1998 |
| WO | WO9851212 | 11/1998 |
| WO | WO9857577 | 12/1998 |
| WO | WO9900053 | 1/1999 |
| WO | WO9932030 | 7/1999 |
| WO | WO9947039 | 9/1999 |
| WO | WO9963884 | 12/1999 |
| WO | WO0021438 | 4/2000 |
| WO | WO0028888 | 5/2000 |
| WO | WO0059374 | 10/2000 |
| WO | WO0113790 | 3/2001 |
| WO | WO0116577 | 3/2001 |
| WO | WO0117421 | 3/2001 |
| WO | WO0147426 | 3/2001 |
| WO | WO0140776 | 6/2001 |
| WO | WO0167946 | 9/2001 |
| WO | WO0176461 | 10/2001 |
| WO | WO0214793 | 2/2002 |
| WO | WO0235999 | 5/2002 |
| WO | WO02062213 | 8/2002 |
| WO | WO02074162 | 9/2002 |
| WO | WO02085202 | 10/2002 |
| WO | WO03000125 | 1/2003 |
| WO | WO03001180 | 1/2003 |
| WO | WO03009750 | 2/2003 |
| WO | WO03011127 | 2/2003 |
| WO | WO03020129 | 3/2003 |
| WO | WO03039326 | 5/2003 |
| WO | WO03063697 | 8/2003 |
| WO | WO03073924 | 9/2003 |
| WO | WO04000114 | 12/2003 |
| WO | WO2004006748 | 1/2004 |
| WO | WO2004069046 | 8/2004 |
| WO | WO2004075746 | 9/2004 |
| WO | WO2005002434 | 1/2005 |
| WO | WO2005009221 | 2/2005 |
| WO | WO2005010567 | 2/2005 |
| WO | WO2005010568 | 2/2005 |
| WO | WO2005020120 | 3/2005 |
| WO | WO2005053530 | 6/2005 |
| WO | WO2005065540 | 7/2005 |
| WO | WO2006005169 | 1/2006 |
| WO | WO2006039752 | 4/2006 |
| WO | WO2006064399 | 6/2006 |
| WO | WO2006104790 | 10/2006 |
| WO | WO2006110488 | 10/2006 |
| WO | WO2007041296 | 4/2007 |
| WO | WO2007041331 | 4/2007 |
| WO | WO2007147343 | 12/2007 |
| WO | WO2008019294 | 2/2008 |
| WO | WO2008020845 | 2/2008 |

OTHER PUBLICATIONS

Zahar et al.; "Automatic Feedback Control of Oxygen Therapy Using Pulse Oximetry" *Annual International Conference of the IEEE Engineering in Medicine and Biology Society* vol. 13 No. 4 pp. 1614-1615 (1991).

Aoyagi T. et al.; "Analysis of Motion Artifacts in Pulse Oximetry," *Japanese Society ME* vol. 42 p. 20 (1993) (Article in Japanese—contains English summary of article).

Barreto et al.; "Adaptive Cancelation of Motion artifact in Photoplethysmographic Blood Volume Pulse Measurements for Exercise Evaluation" *IEEE-EMBC and CMBEC—Theme 4: Signal Processing* pp. 983-984 (1995).

Vicente L.M. et al.; "Adaptive Pre-Processing of Photoplethysmographic Blood Volume Pulse Measurements" pp. 114-117 (1996).

Plummer John L. et al.; "Identification of Movement Artifact by the Nellcor N-200 and N-3000 Pulse Oximeters" *Journal of clinical Monitoring* vol. 13 pp. 109-113 (1997).

Barnum P.T. et al.; "Novel Pulse Oximetry Technology Capable of Reliable Bradycardia Monitoring in the Neonate" *Respiratory Care* vol. 42 No. 1 p. 1072 (Nov. 1997).

Poets C. F. et al.; "Detection of movement artifact in recorded pulse oximeter saturation" *Eur. J. Pediatr.*; vol. 156 pp. 808-811 (1997).

Masin Donald I. et al.; "Fetal Transmission Pulse Oximetry" *Proceedings 19th International Conference IEEE/EMBS* Oct. 30-Nov. 2, 1997; pp. 2326-2329.

Block Frank E. Jr. et al.; "Technology evaluation report: Obtaining pulse oximeter signals when the usual probe cannot be used" *International journal of clinical Monitoring and Computing* vol. 14 pp. 23-28 (1997).

Nijland Roel et al.; "Validation of Reflectance Pulse Oximetry: An Evaluation of a new Sensor in Piglets" *Journal of Clinical Monitoring* vol. 13 pp. 43-49 (1997).

Soto Denise A.; "A Comparative Study of Pulse Oximeter Measurements: Digit Versus Earlobe" Master of Science Thesis California State University Dominguez Hills May 1997 46 pgs.

Faisst Karin et al.; "Intrapartum Reflectance Pulse Oximetry: Effects of Sensor Location and Fixation Duration on Oxygen Saturation Readings" *Journal of Clinical Monitoring* vol. 13 pp. 299-302 (1997).

Izumi Akio et al.; "Accuracy and Utility of a New Reflectance Pulse Oximeter for Fetal Monitoring During Labor" *Journal of Clinical Monitoring* vol. 13 pp. 103-108 (1997).

Mannheimer Paul D. et al.; "Wavelength Selection for Low/Saturation Pulse Oximetry" *IEEE Transactions on Biomedical Engineering* vol. 44 No. 3 pp. 148-158 (Mar. 1997).

"Smaller Product Tighter Tolerances Pose Dispensing Challenges for Medical Device Manufacturer" *Adhesives Age* pp. 40-41 (Oct. 1997).

Buschman J.P. et al.; "Principles and Problems of Calibration of Fetal Oximeters" Biomedizinische Technik vol. 42 pp. 265-266 (1997).

Pickett John et al.; "Pulse Oximetry and PPG Measurements in Plastic Surgery" *Proceedings—19th International Conference—IEEE/EMBS* Chicago Illinois Oct. 30-Nov. 2, 1997 pp. 2330-2332.

Leahy Martin J. et al.; "Sensor Validation in Biomedical Applications" *IFAC Modelling and Control in Biomedical Systems* Warwick UK; pp. 221-226 (1997).

Barreto Armando B. et al.; "Adaptive LMS Delay Measurement in dual Blood Volume Pulse Signals for Non/Invasive Monitoring" *IEEE* pp. 117-120 (1997).

Crilly Paul B. et al.; "An Integrated Pulse Oximeter System for Telemedicine Applications" *IEEE Instrumentation and Measurement Technology Conference* Ottawa Canada; May 19-21, 1997; pp. 102-104.

(56) References Cited

OTHER PUBLICATIONS

DeKock Marc; "Pulse Oximetry Probe Adhesive Disks: a Potential for Infant Aspiration" *Anesthesiology* vol. 89 pp. 1603/1604 (1998).
East Christine E. et al.; "Fetal Oxygen Saturation and Uterine Contractions During Labor" *American Journal of Perinatology* vol. 15 No. 6 pp. 345-349 (Jun. 1998).
Rhee Sokwoo et al.; "The Ring Sensor: a New Ambulatory Wearable Sensor for Twenty-Four Hour Patient Monitoring" *Proceedings of the 20th annual International Conference of the IEEE Engineering in Medicine and Biology Society* vol. 20 No. 4 pp. 1906-1909 (Oct. 1998).
Yang Boo/Ho et al.; "A Twenty/Four Hour Tele-Nursing System Using a Ring Sensor" *Proceedings of the 1998 IEEE International Conference on Robotics & Automation* Leaven Belgium May 1998; pp. 387-392.
König Volker et al.; "Reflectance Pulse Oximetry—Principles and Obstetric Application in the Zurich System" *Journal of Clinical Monitoring and Computing* vol. 14 pp. 403-412 (1998).
Nogawa Masamichi et al.; "A Novel Hybrid Reflectance Pulse Oximeter Sensor with improved Linearity and General Applicability to Various Portions of the Body" *Proceedings of the 20th Annual International Conference of the IEEE Engineering in Medicine and Biology Society* vol. 20 No. 4 pp. 1858-1861 (1998).
Hayes Matthew J. et al.; "Quantitative evaluation of photoplethysmographic artifact reduction for pulse oximetry" *SPIE* vol. 3570 pp. 138-147 (Sep. 1998).
Edrich Thomas et al.; "Can the Blood Content of the Tissues be Determined Optically During Pulse Oximetry Without Knowledge of the Oxygen Saturation?—An In-Vitro Investigation" *Proceedings of the 20th Annual International conference of the IEEE Engineering in Medicine and Biology Society* vol. 20 No. 6 pp. 3072-3075 (1998).
Hayes Matthew J. et al.; "Artifact reduction in photoplethysmography" *Applied Optics* vol. 37 No. 31 pp. 7437-7446 (Nov. 1998).
Such Hans Olaf; "Optoelectronic Non-invasive Vascular Diagnostics Using multiple Wavelength and Imaging Approach" *Dissertation* (1998).
Lutter N. et al.; "Comparison of Different Evaluation Methods for a Multi-wavelength Pulse Oximeter" *Biomedizinische Technik* vol. 43 (1998).
Ferrell T.L. et al.; "Medical Telesensors" *SPIE* vol. 3253 pp. 193-198 (1998).
Todd Bryan et al.; "The Identification of Peaks in Physiological Signals" *Computers and Biomedical Research* vol. 32 pp. 322-335 (1999).
Rhee Sokwoo et al.; "Design of a Artifact-Free Wearable Plethysmographic Sensor" *Proceedings of the First joint BMES/EMBS Conference* Oct. 13-16, 1999 Atlanta, Georgia p. 786.
Rohling Roman et al.; "Clinical Investigation of a New Combined Pulse Oximetry and Carbon Dioxide Tension Sensor in Adult Anaesthesia" *Journal o Clinical Monitoring and Computing* vol. 15; pp. 23-27 (1999).
Ikeda Kenji et al.; "Improvement of Photo-Electric Plethysmograph Applying Newly Developed Opto/Electronic Devices" *IEEE Tencon* pp. 1109-1112 (1999).
Kaestle S.; "An Algorithm for Reliable Processing of Pulse Oximetry Signals Under strong Noise Conditions" *Dissertation Book* Lubeck University Germany (1999).
Seelbach-Göbel Birgit et al.; "The prediction of fetal acidosis by means of intrapartum fetal pulse oximetry" *Am J. Obstet. Gynecol.* vol. 180 No. 1 Part 1 pp. 73-81 (1999).
Yang Boo-Ho et al.; "Development of the ring sensor for healthcare automation" *Robotics and Autonomous Systems* vol. 30 pp. 273-281 (2000).
Rhee Sokwoo et al.; "Artifact-Resistant Power-Efficient Design of Finger-Ring Plethysmographic Sensor—Part I: Design and Analysis" *Proceedings of the 22nd Annual EMBS International Conference* Chicago Illinois; Jul. 23-28, 2000; pp. 2792-2795.
Rhee Sokwoo et al.; "Artifact-Resistant Power-Efficient Design of Finger-Ring Plethysmographic Sensor—Part II: Prototyping and Benchmarking" *Proceedings of the 22nd Annual EMBS International Conference* Chicago Illinois; Jul. 23-28, 2000; pp. 2796-2799.
Vicenzi Martin N.; "Transesophageal versus surface pulse oximetry in intensive care unit patients" *Crit. Care Med.*; vol. 28 No. 7 pp. 2268-2270 (2000).
Goldman Julian M.; "Masimo Signal Extraction Pulse Oximetry" *Journal of Clinical Monitoring and Computing* vol. 16 pp. 475-483 (2000).
Coetzee Frans M.; "Noise-Resistant Pulse Oximetry Using a Synthetic Reference Signal" *IEEE Transactions on Biomedical Engineering* vol. 47 No. 8 Aug. 2000 pp. 1018-1026.
Nilsson Lena et al.; "Monitoring of Respiratory Rate in Postoperative Care Using a New Photoplethysmographic Technique" *Journal of Clinical Monitoring and Computing* vol. 16 pp. 309-315 (2000).
Nijland Mark J.M. et al.; "Assessment of fetal scalp oxygen saturation determination in the sheep by transmission pulse oximetry" *Am. J. Obstet Gynecol.* vol. 183 No. 6 pp. 1549-1553 (Dec. 2000).
Edrich Thomas et al.; "Pulse Oximetry: An Improved in Vitro Model that Reduces Blood Flow-Related Artifacts" *IEEE Transactions on Biomedical Engineering* vol. 47 No. 3 pp. 338-343 (Mar. 2000).
Schulz Christian Eric; "Design of a Pulse Oximetry Sensor Housing Assembly" California State University Master's Thesis *UMI Dissertation Services* UMI No. 1401306 (May 2000) 63 pages.
Yao Jianchu et al.; "Design of a Plug-and-Play Pulse Oximeter" *Proceedings of the Second Joint EMBS/BMES Conference* Houston Texas Oct. 23-26, 2002; pp. 1752-1753.
Aoyagi T. et al.; "Pulse Oximeters: background present and future" *Neonatal Care* vol. 13 No. 7 pp. 21-27 (2000) (Article in Japanese—contains English summary of article).
Yokota Nakaura Takahashi et al.; "Pilot Model of a Reflectance-Type Pulse Oximeter for Pre-hospital Evaluation" *Journal of the Japanese Society of Emergency Medicine* Kanto Region vol. 21 pp. 26-27 (2000) (Article in Japanese—contains English summary of article).
Kaestle S.; "Determining Artefact Sensitivity of New Pulse Oximeters in Laboratory Using Signals Obtained from Patient" *Biomedizinische Technik* vol. 45 (2000).
Cubeddu Rinaldo et al.; "Portable 8-channel time-resolved optical imager for functional studies of biological tissues" *Photon Migration Optical Coherence Tomography and Microscopy Proceedings of SPIE* vol. 4431 pp. 260-265 (2001).
Gisiger P.A. et al.; "OxiCarbo® a single sensor for the non-invasive measurement of arterial oxygen saturation and $CO_2$ partial pressure at the ear lobe" *Sensor and Actuators* vol. B-76 pp. 527-530 (2001).
Cysewska-Sobusaik Anna; "Metrological Problems With noninvasive Transillumination of Living Tissues" *Proceedings of SPIE* vol. 4515 pp. 15-24 (2001).
Rhee Sokwoo et al.; "Artifact-Resistant Power-Efficient Design of Finger-Ring Plethysmographic Sensor" *IEEE Transactions on Biomedical Engineering* vol. 48 No. 7 pp. 795-805 (Jul. 2001).
Belal Suliman Yousef et al.; "A fuzzy system for detecting distorted plethysmogram pulses in neonates and paediatric patients" *Physiol. Meas.* vol. 22 pp. 397-412 (2001).
Hayes Matthew J. et al.; "A New Method for Pulse Oximetry Possessing Inherent Insensitivity to Artifact" *IEEE Transactions on Biomedical Engineering* vol. 48 No. 4 pp. 452-461 (Apr. 2001).
Gosney S. et al.; "An alternative position for the pulse oximeter probe" *Anaesthesia* vol. 56 p. 493 (2001).
Silva-Lopez et al.; "NIR transmittance pulse oximetry system with laser diodes" *Clinical Diagnostic Systems Proceedings of SPIE* vol. 4255 pp. 80-87 (2001).
Maletras Francois-Xavier et al.; "Construction and calibration of a new design of Fiber Optic Respiratory Plethysmograph (FORP)" *Optomechanical Design and Engineering Proceedings of SPIE* vol. 4444 pp. 285-293 (2001).
Earthrowl-Gould T. et al.; "Chest and abdominal surface motion measurement for continuous monitoring of respiratory function" *Proc. Instn Mech Engrs* V215 Part H; pp. 515-520 (2001).
Gehring Harmut et al.; "The Effects of Motion Artifact and Low Perfusion on the Performance of a New Generation of Pulse Oximeters in Volunteers Undergoing Hypoxemia" *Respiratory Care* Vo. 47 No. 1 pp. 48-60 (Jan. 2002).
Jopling et al.; "Issues in the Laboratory Evaluation of Pulse Oximeter Performance" *Anesth Analg* vol. 94 pp. S62-S68 (2002).

(56) References Cited

OTHER PUBLICATIONS

Gostt R. et al.; "Pulse Oximetry Artifact Recognition Algorithm for Computerized Anaesthetic Records" *Journal of Clinical Monitoring and Computing Abstracts* p. 471 (2002).
Chan K.W. et al.; "17.3: Adaptive Reduction of Motion Artifact from Photoplethysmographic Recordings using a Variable Step-Size LMS Filter" *IEEE* pp. 1343-1346 (2002).
Relente A.R. et al.; "Characterization and Adaptive Filtering of Motion Artifacts in Pulse Oximetry using Accelerometers" *Proceedings of the Second joint EMBS/BMES Conference* Houston Texas Oct. 23-26, 2002; pp. 1769-1770.
Yamaya Yoshiki et al.; "Validity of pulse oximetry during maximal exercise in normoxia hypoxia and hyperoxia" *J. Appl. Physiol.* vol. 92 pp. 162-168 (2002).
Lutter Norbert O. et al.; "False Alarm Rates of Three Third-Generation Pulse Oximeters in PACU ICU and IABP Patients" *Anesth Analg* vol. 94 pp. S69-S75 (2002).
Lutter N. et al.; "Accuracy of Noninvasive Continuous Blood Pressure; Measurement Utilising the Pulse Transit Time" *Journal of clinical Monitoring and Computing* vol. 17 Nos. 7-8 pp. 469 (2002).
Liu Ying et al.; "Sensor design of new type reflectance pulse oximetry" *Optics in Health Care and Biomedical Optics: Diagnostics and Treatment Proceedings of SPIE* vol. 4916 pp. 98-102 (2002).
Kyriacou Panayiotis A. et al.; "Esophageal Pulse Oximetry Utilizing Reflectance Photoplethysmography" *IEEE Transactions on Biomedical Engineering* vol. 49 No. 11 pp. 1360-1368 (Nov. 2002).
Kyriacou P. A. et al.; "Investigation of esophageal photoplethysmographic signals and blood oxygen saturation measurements in cardiothoracic surgery patients" *Physiological Measurement* vol. 23 No. 3 pp. 533-545 (Aug. 2002).
Tobata H. et al.; "Study of Ambient Light Affecting Pulse Oximeter Probes" *Ikigaku (Medical Technology)* vol. 71 No. 10 pp. 475-476 (2002) (Article in Japanese—contains English summary of article).
Irie A. et al.; "Respiration Monitors—Pulse Oximeters" *Neonatal Care* vol. 15 No. 12 pp. 78-83 (2002) (Article in Japanese—contains English summary of article).
Koga I. et al.; "Sigmoid colonic reflectance pulse oximetry and tonometry in a porcine experimental hypoperfusion shock model" *Acta Anaesthesiol Scand* vol. 46 pp. 1212-1216 (2002).
Shaltis Phillip et al.; "Implementation and Validation of a Power-Efficient, High-Speed Modulation Design for Wireless Oxygen Saturation Measurement Systems" *IEEE* pp. 193-194 (2002).
Warren Steve et al.; "Wearable Sensors and Component-Based Design for Home Health Care" *Proceedings of the Second Joint EMBS/BMES Conference* Houston Texas; Oct. 23-26, 2002; pp. 1871-1872.
Ericson M.N. et al.; "In vivo application of a minimally invasive oximetry based perfusion sensor" *Proceedings of the Second Joint EMBS/BMES Conference* Houston Texas; Oct. 23-26, 2002 pp. 1789-1790.
Yoon Gilwon et al.; Multiple diagnosis based on Photo/plethysmography: hematocrib SpO2 pulse and respiration *Optics in Health Care and Biomedical optics: Diagnostics and Treatment; Proceedings of the SPIE* vol. 4916; pp. 185-188 (2002).
Hase Kentaro et al.; "Continuous Measurement of Blood Oxygen Pressure Using a Fiber Optic Sensor Based on Phosphorescense Quenching" *Proceedings of the Second Joint EMBS/BMES Conference* Houston Texas; Oct. 23-26, 2002 pp. 1777-1778.
Pothisarn W. et al.; "A non-invasive hemoglobin measurement based pulse oximetry" *Optics in Health Care and Biomedical Optics: Diagnostics and Treatment; Proceedings of SPIE* vol. 4916; pp. 498-504 (2002).
Tremper K.K.; "A Second Generation Technique for Evaluating Accuracy and Reliability of Second Generation Pulse Oximeters" *Journal of Clinical Monitoring and Computing* vol. 16 pp. 473-474 (2002).
Silva Sonnia Maria Lopez et al.; "Near-infrared transmittance pulse oximetry with laser diodes" *Journal of Biomedical Optics* vol. 8 No. 3 pp. 525-533 (Jul. 2003).

Cyrill D. et al.; "Adaptive Comb Filter for Quasi-Periodic Physiologic Signals" *Proceedings of the 25th Annual International Conference of the IEEE EMBS* Cancun Mexico Sep. 17-21, 2003; pp. 2439-2442.
Matthews Nora S. et al.; "An evaluation of pulse oximeters in dogs, cats and horses" *Veterinary Anaesthesia and Analgesia* vol. 30 pp. 3-14 (2003).
Stetson Paul F.; "Determining Heart Rate from Noisey Pulse Oximeter Signals Using Fuzzy Logic" *The IEEE International Conference on Fuzzy Systems* St. Louis Missouri May 25-28, 2003; pp. 1053-1058.
Aoyagi Takuo; "Pulse oximetry: its invention, theory, and future" *Journal of Anesthesia* vol. 17 pp. 259-266 (2003).
Avidan A.; "Pulse oximeter ear probe" *Anaesthesia* vol. 58 pp. 726 (2003).
Lee C.M. et al.; "Reduction of motion artifacts from photoplethysmographic recordings using wavelet denoising approach" *IEEE EMBS Asian-Pacific Conference on Biomedical Engineering* Oct. 20-22, 2003; pp. 194-195.
Mendelson Y. et al.; "Measurement Site and Photodetector Size Considerations in Optimizing Power Consumption of a Wearable Reflectance Pulse Oximeter" *Proceedings of the 25th Annual International conference of the IEEE EMBS* Cancun Mexico Sep. 17-21, 2003; pp. 3016-3019.
Itoh K. et al.; "Pulse Oximeter" *Toyaku Zasshi* (Toyaku Journal) vol. 25 No. 8 pp. 50-54 (2003) (Article in Japanese—contains English summary of article).
Matsui A. et al.; "Pulse Oximeter" *Neonatal Care* vol. 16 No. 3 pp. 38-45 (2003) (Article in Japanese—contains English summary of article).
Nakagawa M. et al.; "Oxygen Saturation Monitor" *Neonatal Monitoring* vol. 26 No. 5 pp. 536-539 (2003) (Article in Japanese—contains English summary of article).
Kubota H. et al.; "Simultaneous Monitoring of PtcCO2 and SpO2 using a Miniature earlobe sensor" *Jinko Kokyo (Aritificial Respiration)* vol. 20 No. 1 pp. 24-29 (2003).
Lebak J.W. et al.; "Implementation of a Standards-Based Pulse Oximeter on a Wearable Embedded Platform" *Proceeding of the 25th Annual International Conference of the IEEE EMBS* Cancun Mexico Sep. 17-21, 2003; pp. 3196-3198.
Nagl L. et al.; "Wearable Sensor System for Wireless State-of-Health Determination in Cattle" *Proceeding of the 25th Annual International Conference of the IEEE EMBS* Cancun Mexico Sep. 17-21, 2003; pp. 3012-3015.
Östmark Åke et al.; "Mobile Medical Applications Made Feasible Through Use of EIS Platforms" *IMTC—Instrumentation and Measurement Technology Conference* Vail Colorado; May 20-22, 2003; pp. 292-295.
Warren Steve et al.; "A Distributed Infrastructure for Veterinary Telemedicine" *Proceedings of the 25th Annual International Conference of the IEEE EMBS* Cancun Mexico; Sep. 17-21, 2003; pp. 1394-1397.
Pujary C. et al.; "Photodetector Size Considerations in the Design of a Noninvasive Reflectance Pulse Oximeter for Telemedicine Applications" *IEEE* pp. 148-149 (2003).
A. Johansson; "Neural network for photoplethysmographic respiratory rate monitoring" *Medical & Biological Engineering & Computing* vol. 41 pp. 242-248 (2003).
Reuss James L.; "Factors Influencing Fetal Pulse Oximetry Performance" *Journal of clinical Monitoring and Computing* vol. 18 pp. 13-14 (2004).
Mannheimer Paul D. et al.; "The influence of Larger Subcutaneous Blood Vessels on Pulse Oximetry" *Journal of clinical Monitoring and Computing* vol. 18 pp. 179-188 (2004).
Wendelken Suzanne et al.; "The Feasibility of Using a Forehead Reflectance Pulse Oximeter for Automated Remote Triage" *IEEE* pp. 180-181 (2004).
Lopez-Silva S.M. et al.; "Transmittance Photoplethysmography and Pulse Oximetry With Near Infrared Laser Diodes" *IMTC 2004—Instrumentation and Measurement Technology Conference* Como Italy May 18-20, 2004; pp. 718-723.

(56) References Cited

OTHER PUBLICATIONS

Sugino Shigekzau et al.; "Forehead is as sensitive as finger pulse oximetry during general anesthesia" *Can J. Anesth.; General Anesthesia* vol. 51 No. 5; pp. 432-436 (2004).

Addison Paul S. et al.; "A novel time-frequency-based 3D Lissajous figure method and its application to the determination of oxygen saturation from the photoplethysmogram" *Institute of Physic Publishing Meas. Sci. Technol.* vol. 15 pp. L15-L18 (2004).

Jovanov E. et al.; "Reconfigurable intelligent Sensors for Health Monitoring: A case Study of Pulse Oximeter Sensor" *Proceedings o the 26th Annual International conference of the IEEE EMBS* San Francisco California Sep. 1-5, 2004 pp. 4759-4762.

Kocher Serge et al.; "Performance of a Digital $PCO_2/SPO_2$ Ear Sensor" *Journal of Clinical Monitoring and Computing* vol. 18 pp. 75-59 (2004).

Yao Jianchu et al.; "A Novel Algorithm to Separate Motion Artifacts from Photoplethysmographic Signals Obtained With a Reflectance Pulse Oximeter" *Proceedings of the 26th Annual International conference of the IEEE EMBS* San Francisco California Sep. 1-5, 2004; pp. 2153-2156.

Nuhr M. et al.: "Forehead $SpO_2$ monitoring compared to finger $SpO_2$ recording in emergency transport" *Anaesthesia* vol. 59 pp. 390-393 (2004).

Johnston William S. et al.; "Effects of Motion Artifacts on helmet-Mounted Pulse Oximeter Sensors" 2 pgs. (2004).

Branche Paul C. et al.; "Measurement Reproducibility and Sensor Placement Considerations in Designing a Wearable Pulse Oximeter for Military Applications" 2 pgs. (2004).

Kocher Serge et al.; "Performance of a Digital $PCO_2/SPO_2$ Ear Sensor" *Journal of Clinical Monitoring and Computing* vol. 18 pp. 75-79 (2004).

Heuss Ludwig T. et al.; "Combined Pulse Oximetry / Cutaneous Carbon dioxide Tension Monitoring During Colonoscopies: Pilot study with a Smart Ear Clip" *Digestion* vol. 70 pp. 152-158 (2004).

Matsuzawa Y. et al.; "Pulse Oximeter" *Home Care Medicine* pp. 42-45 (Jul. 2004); (Article in Japanese—contains English summary of article).

Crespi F. et al.; "Near infrared oxymeter prototype for non-invasive analysis of rat brain oxygenation" *Optical Sensing Proceedings of SPIE* vol. 5459 pp. 38-45 (2004).

Johnston W.S. et al.; "Extracting Breathing Rate Information from a Wearable Reflectance Pulse Oximeter Sensor" *Proceedings of the 26th Annual International conference of the IEEE EMBS* San Francisco California; Sep. 1-5, 2004; pp. 5388-5391.

Spigulis Janis et al.; "Optical multi-channel sensing of skin blood pulsations" *Optical Sensing Proceedings of SPIE* vol. 5459 pp. 46-53 (2004).

Yan Yong-sheng et al.; "Reduction of motion artifact in pulse oximetry by smoothed pseudo Wigner-Ville distribution" *Journal of NeuroEngineering and Rehabilitation* vol. 2 No. 3 (9 pages) (Mar. 2005).

Urquhart C. et al.; "Ear probe pulse oximeters and neonates" *Anaesthesia* vol. 60 p. 294 (2005).

J. Hayoz et al.; "World's First Combined digital Pulse Oximetry Pulse Oximetry and Carbon Dioxide Tension Ear Sensor" *Abstracts* A6 p. S103. (2002).

J. Huang et al.; "Low Power Motion Tolerant Pulse Oximetry" *Abstracts* A7 p. S103. (2002).

P. Lang et al.; "Signal Identification and Quality Indicator™ for Motion Resistant Pulse Oximetry" *Abstracts* A10 p. S105. (undated).

Hamilton Patrick S. et al.; "Effect of Adaptive Motion-Artifact Reduction on QRS Detection" *Biomedical Instrumentation & Technology* pp. 197-202 (undated).

Kim J.M. et al.; "Signal Processing Using Fourier & Wavelet Transform" pp. II-310-II-311 (undated).

Lee C.M. et al.; "Reduction of Motion Artifacts from Photoplethysmographic Records Using a Wavelet Denoising Approach" *IEEE* pp. 194-195 (undated).

Nogawa Masamichi et al.; "A New Hybrid Reflectance Optical Pulse Oximetry Sensor for Lower Oxygen Saturation Measurement and for Broader Clinical Application" *SPIE* vol. 2976 pp. 78-87 (1997).

Odagiri Y.; "Pulse Wave Measuring Device" *Micromechatronics* vol. 42 No. 3 pp. 6-11 (undated) (Article in Japanese—contains English summary of article).

Yamazaki Nakaji et al.; "Motion Artifact Resistant Pulse Oximeter (Durapulse PA 2100)" *Journal of Oral Cavity Medicine* vol. 69 No. 4 pp. 53 (date unknown) (Article in Japanese—contains English summary of article).

MEDICAL SENSOR FOR REDUCING SIGNAL ARTIFACTS AND TECHNIQUE FOR USING THE SAME

CROSS-REFERENCE TO RELATED APPLICATIONS

This application is a continuation of and claims priority to U.S. patent application Ser. No. 11/507,814, filed on Aug. 22, 2006, which is incorporated herein by reference in its entirety for all purposes.

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits electromagnetic radiation, such as light, through a patient's tissue and that photoelectrically detects the absorption and scattering of the transmitted light in such tissue. One or more of the above physiological characteristics may then be calculated based upon the amount of light absorbed and scattered. More specifically, the light passed through the tissue is typically selected to be of one or more wavelengths that may be absorbed and scattered by the blood in an amount correlative to the amount of the blood constituent present in the tissue. The measured amount of light absorbed and scattered may then be used to estimate the amount of blood constituent in the tissue using various algorithms.

Pulse oximetry readings measure the pulsatile changes in amount and type of blood constituents in tissue. Other events besides the pulsing of arterial blood may lead to modulation of the light path, direction, and the amount of light detected by the sensor, creating potential error in these measurements. Current pulse oximetry techniques may be sensitive to movement, and various types of motion may cause artifacts that may obscure the blood constituent signal. In the emergency room, critical care, intensive care, and trauma center settings, where pulse oximetry is commonly used for patient monitoring, the wide variety of sources of signal artifacts may include moving of a patient or the sensor by healthcare workers, physical motion of an unanaesthetised or ambulatory patient, shivering, seizures, agitation, response to pain and loss of neural control. These motions can have similar frequency content to the pulse, and may lead to similar or even larger optical modulations than the pulse.

Two categories of pulse oximetry sensors in common use may be classified by their pattern of use: the disposable sensor and the reusable sensor. Disposable sensors are typically flexible bandage-type structures that may be attached to the patient with adhesive materials, providing a contact between the patient's skin and the sensor components. Disposable sensors have multiple advantages, including ease of conformation to the patient. The flexible nature of disposable sensors further renders them susceptible to signal artifacts caused by mechanical deformation of the sensor, which changes the amount of light detected. Reusable sensors, often semi-rigid or rigid clip-type devices, are also vulnerable to signal artifacts, such as artifacts caused by partial opening of the clip in response to patient motion. Both categories of sensors may have modulations of detected light induced by the physical motion of the sensor components with respect to each other and the tissue.

Signal artifacts may sometimes be addressed by signal processing and filtering to mitigate the effects of motion after the motion has occurred. However, it would be desirable to provide a sensor that reduces the occurrence of events that may lead to signal artifacts.

SUMMARY

Certain aspects commensurate in scope with the originally claimed invention are set forth below. It should be understood that these aspects are presented merely to provide the reader with a brief summary of certain forms that the invention might take and that these aspects are not intended to limit the scope of the invention. Indeed, the invention may encompass a variety of aspects that may not be set forth below.

There is provided a sensor that includes: a sensor body; at least one sensing element disposed on the sensor body; and at least one rigid annular structure adapted to be removably applied to the sensor body.

There is also provided a physiologic monitoring system that includes: a pulse oximetry monitor; and a pulse oximetry sensor adapted to be operatively coupled to the monitor. The sensor includes: a sensor body; at least one sensing element disposed on the sensor body; and at least one rigid annular structure adapted to be removably applied to the sensor body.

There is also provided a method of operating a sensor that includes: deflecting mechanical force with a rigid annular structure dispersed around an emitter and a detector of a sensor applied to a patient, wherein the rigid annular structure is removably applied to the sensor.

There is also provided a method of manufacturing a sensor that includes: providing sensor body; providing at least one sensing element disposed on the sensor body; and providing at least one rigid annular structure adapted to be removably applied to the sensor body.

There is also provided a kit that includes: a sensor body; an emitter and a detector disposed on the sensor body; and a plurality of rigid annular structures of various sizes adapted to be removably applied to the sensor body.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

Figure 1:
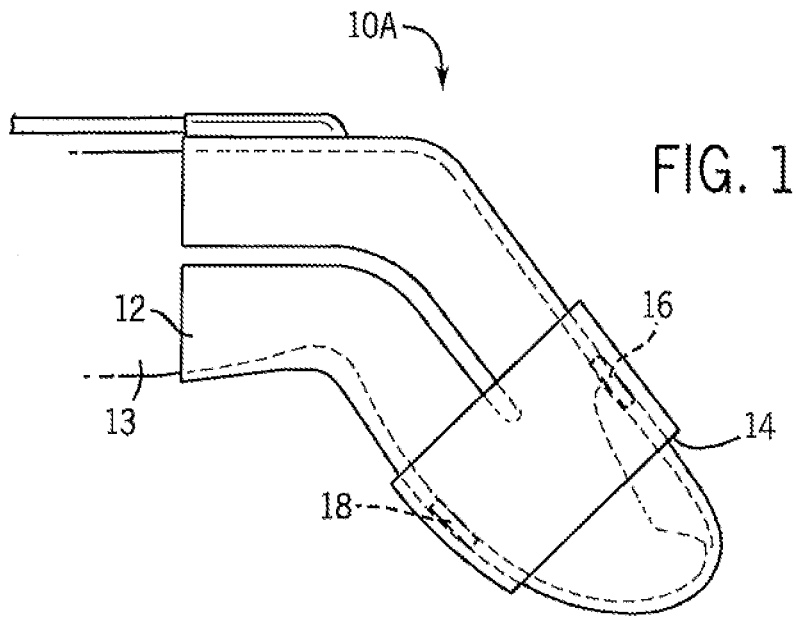
FIG. 1 illustrates a side view of an exemplary bandage-style sensor with a removable ring structure applied to a patient's finger.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In accordance with the present technique, sensors for pulse oximetry or other applications utilizing spectrophotometry are provided that reduce signal artifacts by reducing sensor deformation in response to movement. For example, sensors are provided that have various removable rigid annular structures adapted to reduce the effect of motion or outside forces on sensor measurements by deflecting such forces away from the sensing components and/or preventing movement of the sensing components relative to one another. Such rigid annular structures provide multiple advantages. For example, they are relatively inexpensive, are easy to apply to a patient, and may be made in multiple sizes to accommodate differences in patient anatomy.

Signal artifacts in pulse oximetry are often generated by the movement of the pulse oximetry sensor relative to the optically probed tissue, which is typically caused by patient movement. Because pulse oximetry is often used in settings where it is difficult to prevent patient motion, it is desirable to provide a mechanism for reducing the effects of motion on the pulse oximetry measurement. Generally, sensors are vulnerable to motion artifacts when the optical distance between a sensor's emitter and detector varies due to an undesired mechanical change in the conformation of the sensor while in use.

A change in optical distance may include any change in position or geometry of the emitter and/or the detector relative to the tissue or relative to each other. More specifically, a change in optical distance may involve a change in the path length, a change in the angle of the emitter or detector relative to one another, and/or a change in the angle of the emitter or detector relative to the tissue. For example, signal artifacts may be caused by moving a sensor in relation to the tissue, by increasing or decreasing the physical distance between emitters and detectors in a sensor, by changing the direction of emitters or detectors with respect to tissue or each other, by changing the angles of incidence and interfaces probed by the light, by directing the optical path through different amounts or types of tissue, or by expanding, compressing or otherwise altering tissue near a sensor. A tapping or pressing motion by a patient may serve to compress a flexible bandage sensor, decreasing the path length between the emitter and detector. A jerking or flexing motion may separate the emitter and detector, thus increasing the optical path length. Additionally, any of the above motions may twist or bend the sensor, causing the angle of the emitter and/or the detector to change relative to the sensor and each other. As sensors do not typically emit nor detect light omnidirectionally, any motions that lead to variations in angle of sensor components may alter the amount of light detected, and may force detected light through different portions of tissue. In any case, variability in the optical path length due to motion can cause motion artifacts and obscure the desired pulse oximetry signal. Thus, it is desirable to reduce the effects of patient movement and outside forces on a sensor's emitter and detector such that their movement relative to one another is reduced.

By deflecting forces away from the sensing components such that the effective force experienced by the sensing components may be mitigated, the sensors provided herein limit the modulations of detected light that may occur and the resulting measurement errors. These sensors substantially reduce the occurrence of motion artifacts by minimizing the effects of outside forces or patient motion on the sensing components of the sensor.

Sensors are disclosed herein having removable rigid structures to reduce the effect of motion or outside forces on the measurements of physiological parameters, such as pulse oximetry measurements. Such rigid structures are generally annular, and may include structures that are partially annular, e.g. unclosed semicircular or partial ring structures. The rigid annular structures may be adapted for use on any patient digit, or may be adapted to be used on any other patient tissue, such as a foot, hand, or wrist, that may accommodate an annular structure.

The rigid annular structures may be formed from plastic, polymeric material, metal, wood, composites or any other suitable rigid material. For example, the annular structures may generally hold their shape with forces equal to or greater than 100 grams. In certain embodiments, it may be advantageous to provide lightweight, disposable rigid annular structures for use with disposable bandage-type sensors. In other embodiments, the rigid annular structures may be reusable. In such an embodiment, it may be advantageous to provide rigid annular structures that may be easily cleaned. In specific embodiments, the rigid annular structures may include additional non-rigid motion damping components, such as one or more spring or a foam layer, in order to enhance their motion-deflecting properties.

FIG. 1 illustrates an exemplary bandage-type sensor 10A applied to a patient's digit 13. The sensor 10A has a removable ring 14 disposed on the sensor body 12. The sensor 10A is adapted to be placed onto the patient digit 13, and may be further secured by a bandage or adhesive. The removable ring 14 is a rigid annular structure that may deflect a force that may otherwise result in an emitter 16 and detector 18 moving relative to one another. When a patient scratches or taps using the digit 13, the removable ring 14 deflects the force of the motion by spreading the force equally around the removable ring 14, which results in a reduction of the effects of the motion on the emitter 16 and the detector 18. The removable ring 14 may be of any suitable diameter to provide a fit for the patient's digit 13. Further, the removable ring may be of any suitable width. A ring may be only so wide as to cover 10% or less of the exterior (i.e. not in contact with the tissue when applied) surface area of the sensor body 12 when applied. In alternate embodiments, it may be advantageous for the ring to be wider, and to cover greater than 20%, greater than 30%, or greater than 50% of the exterior surface area of the sensor body 12 when applied. Wider rings may deflect forces over a broader area of the sensor.

Figure 2:
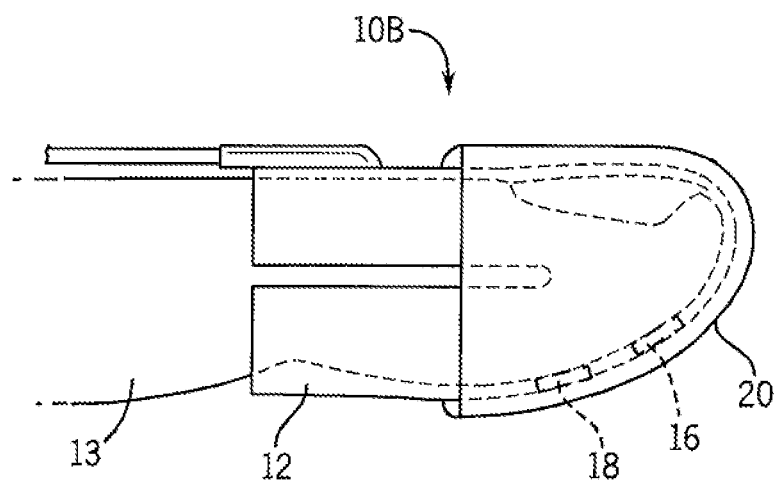
FIG. 2 illustrates a side view of an exemplary bandage-style sensor with a removable thimble structure applied to a patient's finger.

FIG. 2 illustrates an alternative embodiment of a sensor 10B in which the rigid annular structure is a removable thimble 20 that may be applied to a sensor body 12 in order to mechanically stabilize the emitter 16 and the detector 18 after application of the sensor 10B. The thimble 20 may be slid over the fingertip after the sensor body 12 has been applied to the digit. The thimble 20 may be generally useful for deflecting motion caused by tapping with the fingertip.

Figure 3:
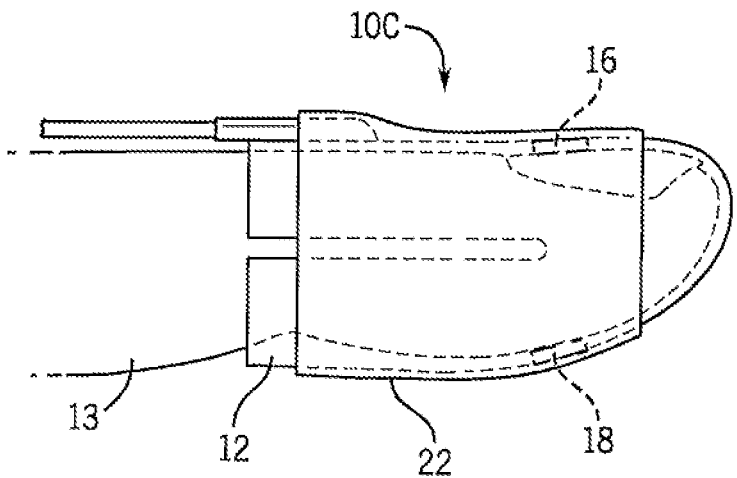
FIG. 3 illustrates a side view of an exemplary bandage-style sensor with a removable sleeve structure applied to a patient's finger.

FIG. 3 illustrates an alternate embodiment of a sensor 10C in which the rigid annular structure is a sleeve 22 that may be applied to a sensor body 12 in order to mechanically stabilize the distance between the emitter 16 and detector 18 after application of the sensor 10C. The sleeve 22 may be removably applied to a digit after the sensor body 12 is in place. The sleeve 22 may, in certain embodiments, cover a finger joint to prevent bending or flexing. In such an embodiment, the removable sleeve 22 may provide the further advantage of adding rigidity to a relatively flexible bandage-style sensor without adding the cost associated with reusable clip-style sensors.

Figure 4:
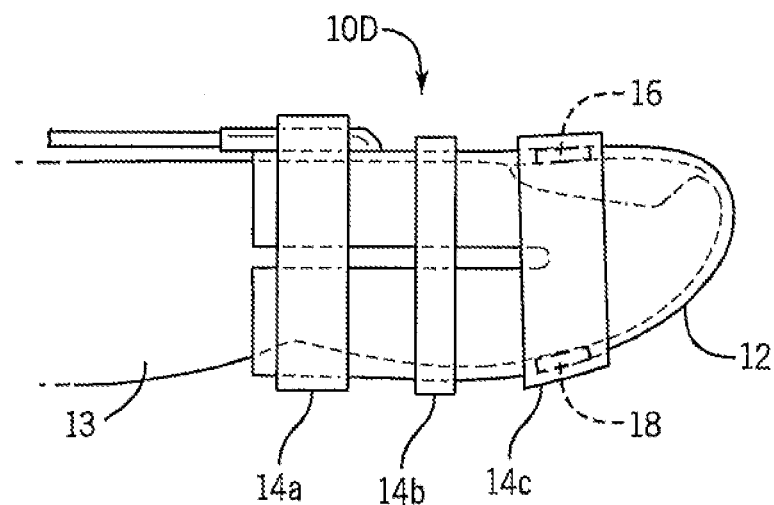
FIG. 4 illustrates a side view of an exemplary bandage-style sensor with multiple removable ring structures applied to a patient's finger.

In certain embodiments, it may be advantageous to apply several annular structures to a sensor body in order to deflect mechanical forces at different locations. FIG. 4 illustrates an embodiment of a sensor 10D in which rings 14a, 14b, and 14c have been applied to the sensor body 12. The ring 14c has been placed directly over the area of the sensor body 12 that includes the emitter 16 and the detector 18. Rings 14a and 14b are placed over areas of the sensor body 12 closer to the joint of the digit 13. Such an arrangement provides the opportunity to minimize forces acting over a wide portion of the sensor body 12 while maintaining a relatively lightweight and flexible sensor structure. In an alternative embodiment (not shown), the rings 14 may be connected to one another by one or more elongated strips to provide additional stability to the sensor assembly while maintaining a relatively lightweight structure. In other embodiments, such elongated strips may provide the advantage of holding the rings in position relative to one another, and may be rigid or relatively flexible to allow the finger to flex or bend slightly.

Figure 5:
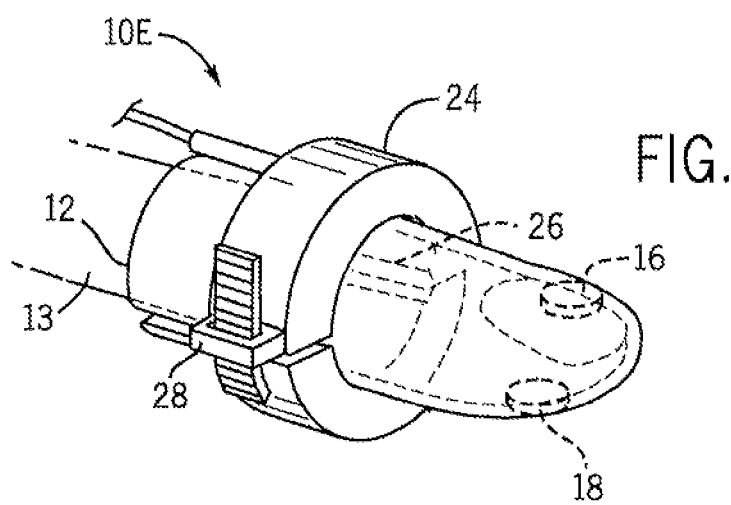
FIG. 5 illustrates a perspective view of an exemplary bandage-style sensor with an adjustable-diameter ring structure with a hinge applied to a patient's finger.

In order to achieve a more conforming fit for an annular structure as provided herein, it may be advantageous to provide sensors that include annular structures with adjustable diameters, as shown in FIG. 5. A sensor 10E has an adjustable ring 24 placed on the sensor body 12. The adjustable ring 24 may open at a hinge 26 and may be adjusted with a strap 28. The adjustable ring 24 may be sized to fit over a fingertip section of the patient's digit 13, which may include the emitter 16 and the detector 18, or may be adjusted to fit over the relatively broader joint section of the patient's digit 13.

Figure 6:
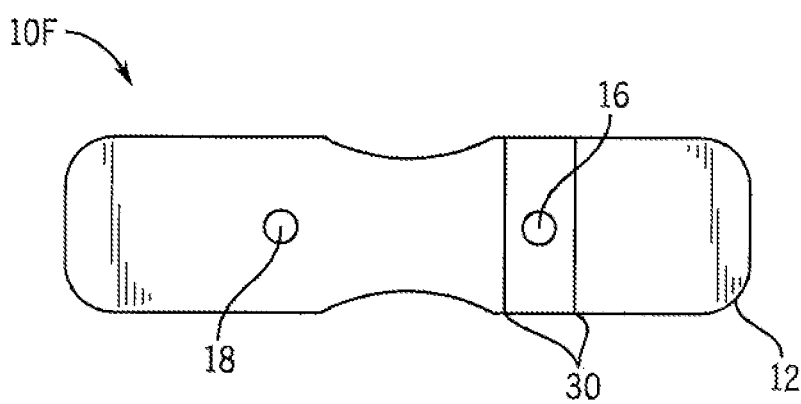
FIG. 6 illustrates a top view of an exemplary embodiment of a bandage-style sensor with alignment indicia to indicate placement for a ring structure.

As shown in FIG. 6, bandage-style sensors as provided herein may include alignment indices to indicate the proper placement of an annular structure on the sensor body. A sensor 10F is shown with alignment indices 30 that provide an indication of proper placement of a ring or other annular structure on the sensor body 12. In order to reduce the effects of motion on a sensor signal, it is advantageous to prevent such motion from disturbing the position of the emitter 16 and the detector 18 relative to one another. Thus, in certain embodiments, the alignments indices may indicate placement of an annular structure over a portion of the sensor body 12 that includes the emitter 16 and the detector 18.

Figure 7A:
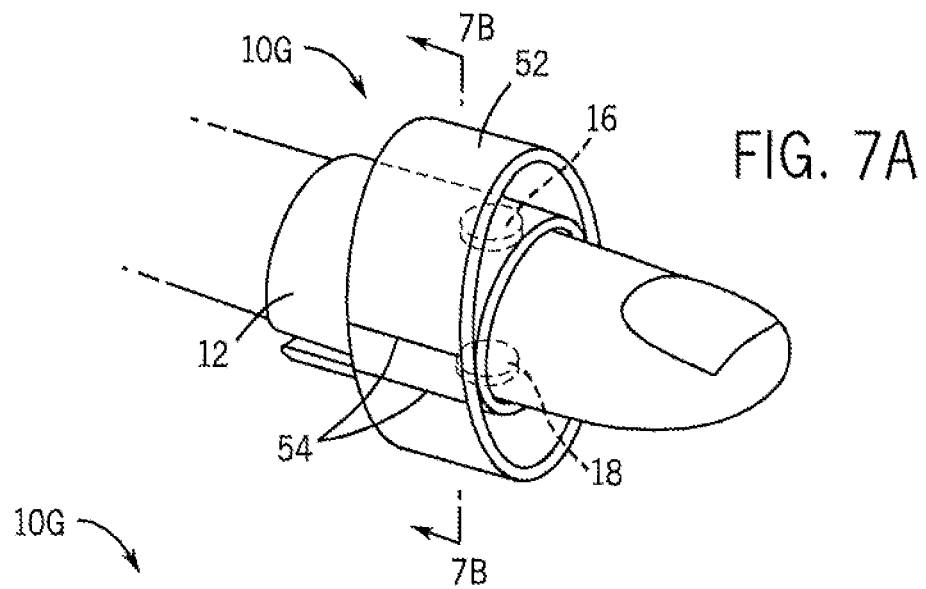
FIG. 7A illustrates a perspective view of an exemplary embodiment of a bandage-style sensor with an oval annular structure that contacts the sensor at the sides of the finger.
Figure 7B:
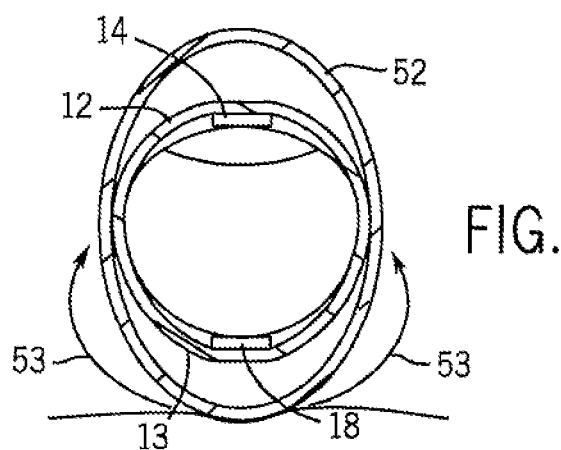
FIG. 7B illustrates a cross-sectional view of the sensor and oval annular structure of FIG. 7A.

In certain embodiments, it may be advantageous to provide an annular structure that does not closely conform to the digit. For example, a sensor 10G with an annular structure 52 shown in FIG. 7A and FIG. 7B only touches the digit 13 in certain areas. The sensor 10G includes an oval annular structure 52 that is adapted to be placed on the digit 13 over a sensor body 12. The annular structure 52 conforms closely to the sides of the digit 13, but does not touch the top or bottom of the digit 13. The annular structure 52 may include alignment indices 54 indicating the portions of the annular structure 52 corresponding to sides of the digit. Thus, a patient or healthcare worker is alerted to the proper placement of the annular structure on the sensor body 12. Such an arrangement of the annular structure 52 over the sensor body 12 tends to spread forces away from the emitter 16 and the detector 18. For example, if the digit 13 engages in a downward tapping motion, the annular structure 52 spreads the force of the motion around its structure. As the annular structure 52 only touches the digit 13 on the sides of the digit 13, the impact of the downward tapping force, shown by arrows 53 in FIG. 7B, is concentrated on the sides of digit 13, and thus the impact is generally directed away from the emitter 16 and the detector 18.

Figure 8:
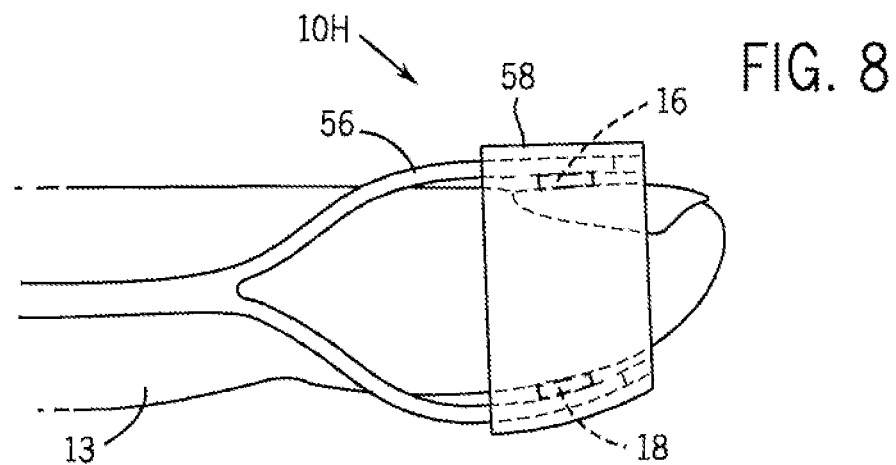
FIG. 8 illustrates a side view of an exemplary embodiment of a Y-style sensor with an annular structure.

As shown in FIG. 8, annular structures as provided herein may be used with any appropriate sensor, including Y-style sensors or other cable sensors. As depicted, a sensor 10H includes a flexible Y-style cable 56 with an emitter 16 and a detector 18. An annular structure 58 may be slid over the Y-style cable 56 after it has been placed on the digit 13. The annular structure 58 not only serves to deflect forces away from the emitter 16 and the detector 18, but may also help hold the Y-style cable 56 in place.

Figure 9:
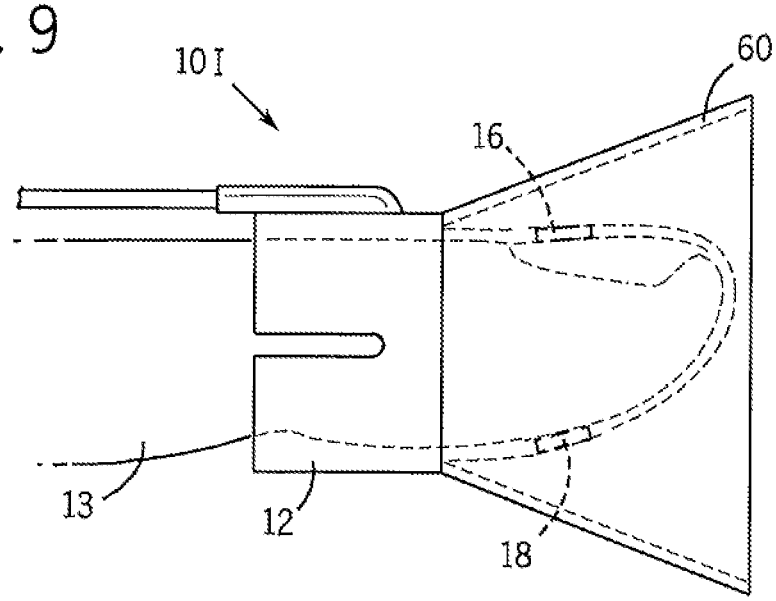
FIG. 9 illustrates a side view of an exemplary embodiment of a bandage-style sensor with an annular structure including a collar.

FIG. 9 shows an alternate embodiment of a sensor 10I with a collar structure 60 that is generally in the shape of an Elizabethan-style collar that substantially encircles the fingertip region. The collar structure may be slid over the sensor body 12 and acts as a guard to prevent motion of the digit 13.

A patient wearing such a sensor 101 may momentarily forget the presence of the sensor 101 and attempt to scratch or otherwise move the digit 13. The presence of the collar structure 60 may prevent the patient from being able to vigorously move the digit 13.

Figure 10:
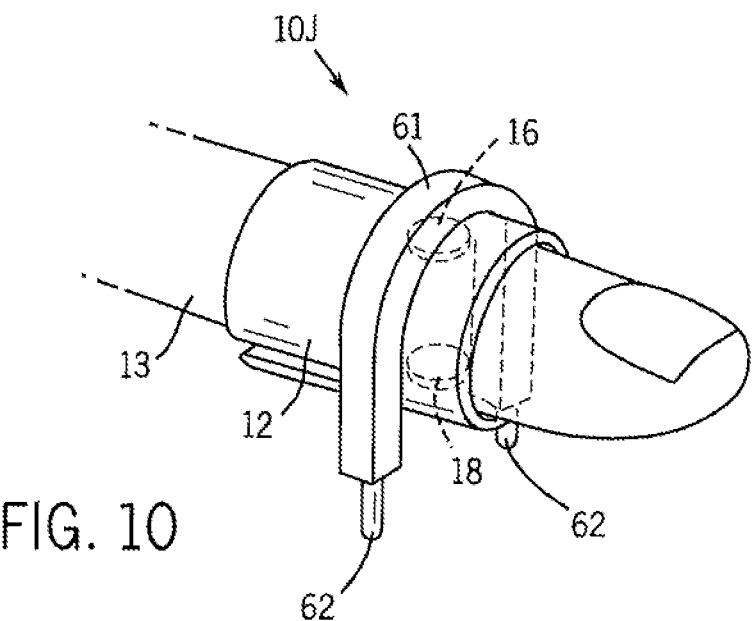
FIG. 10 illustrates a perspective view of an exemplary embodiment of a bandage-style sensor with an arched semi-annular structure.

FIG. 10 shows an alternate embodiment of a sensor 10J that includes an arch structure 61 with protruding prongs 62. The arch structure 61 may be placed over the digit such that the protruding prongs extend in the direction most likely to experience outside forces. For example, during surgery, a patient may be positioned with the palm of the hand facing up. In such an embodiment, the arch structure 61 may be placed over the sensor body 12 such that the protruding prongs 62 are directed away from the palm and towards an operating table or other surface. Alternatively, an active patient may place the arch structure 61 such that the protruding prongs 62 face towards the palm to absorb forces from scratching or tapping. In the event of a downward tapping motion, the prongs 62 may deflect the motion of tapping, spreading much of the impact through the arch structure 61 and away from the emitter 16 and the detector 18. The protruding prongs 62 may be rigid, or may include motion damping structures such as springs (not shown).

Figure 11:
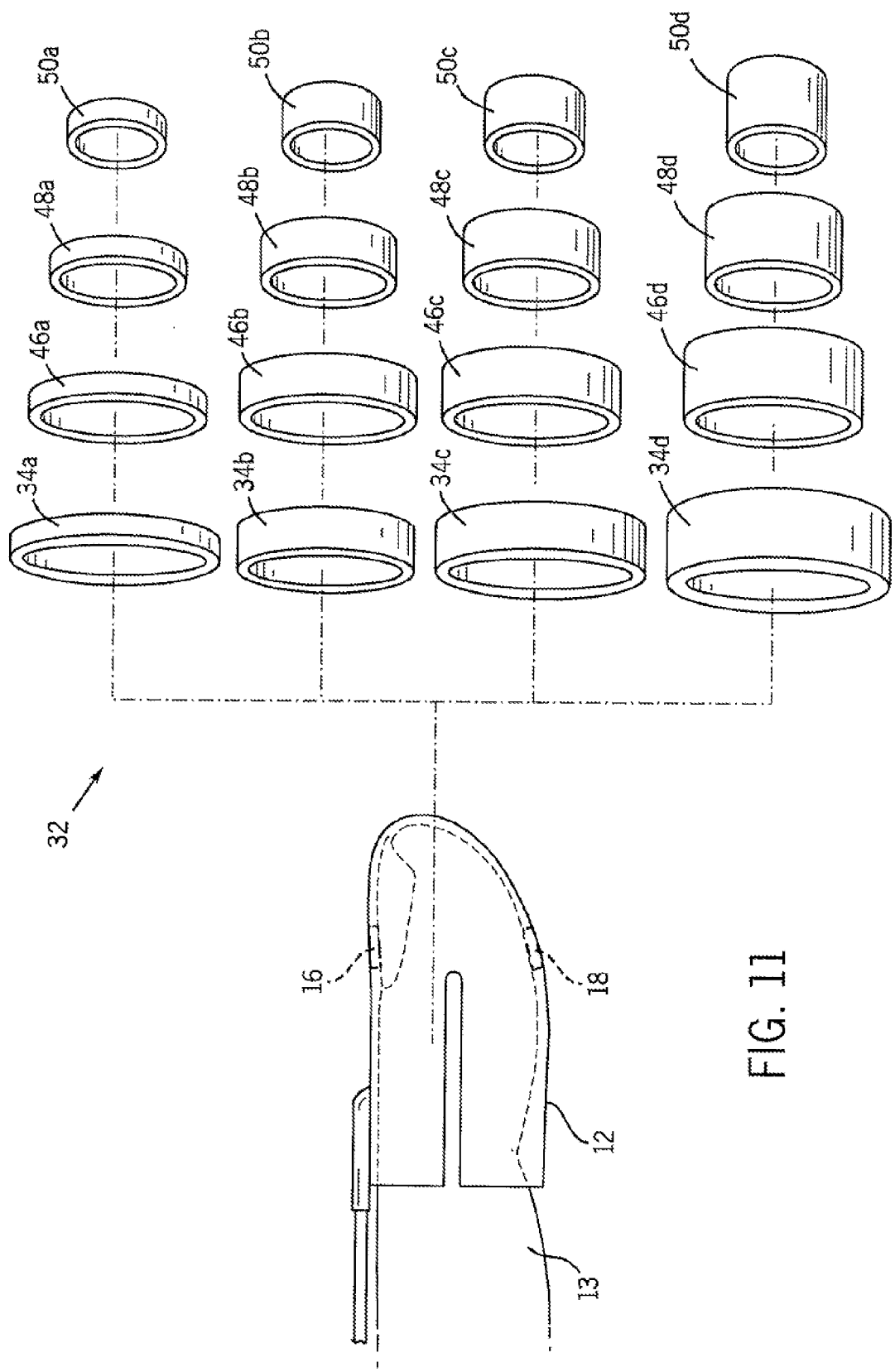
FIG. 11 illustrates a perspective view of a kit including a bandage-style sensor and multiple ring structures of different diameters and widths.

FIG. 11 shows a kit 32 that includes a sensor body 12 and multiple rings 34, 46, 48, and 50. It should be understood that the depicted embodiment of a kit 32 including is merely exemplary, and a kit 32 may include any suitable number of rings 34, 46, 48, and 50 or any other rigid annular structure as provided herein. In one embodiment, the rings 34, 46, 48, and 50 may be of a variety of sizes, which may include a variety of diameters, profiles, and/or widths. In certain embodiments, a kit 32 may include a subsection of sizes that generally correspond to sizes appropriate for a certain type of patient, such as an adult or a child. In one embodiment, the rings 34, 46, 48, and 50 may have different diameters that are sized to correspond with standard jewelry sizes of rings. A healthcare provider or patient may select the appropriately sized ring to apply to the sensor body 12. For example, an individual ring 34 (such as 34a) may be selected from a group having different diameters for having the characteristics of providing a conforming, but not overly tight, fit over the portion of the sensor body 12 that contains the emitter 16 and the detector 18. In other embodiments, a ring may be wider, such as the range of widths shown in rings 34a, 34b, 34c, and 34d. In certain embodiments, it may be advantageous to select a wider ring 34d or 50d (depending on the ring diameter needed) that covers a greater percentage of the sensor body 12 when the patient is non-ambulatory, as a wider ring 34d may mitigate forces along more of the sensor body 12. However, an ambulatory patient may prefer a narrower ring such as 34a or 50a that does not prevent flexing of the finger joint. In another embodiment (not shown), the kit 32 may include rings of a variety of different colors and/or decorative patterns. Such an embodiment may provide enjoyment for a young patient, who may be allowed to select a ring of a preferred color or pattern. Additionally, colored and/or patterned rings may be used in a nursery to identify infants by gender or other clinical characteristics.

Figure 12:
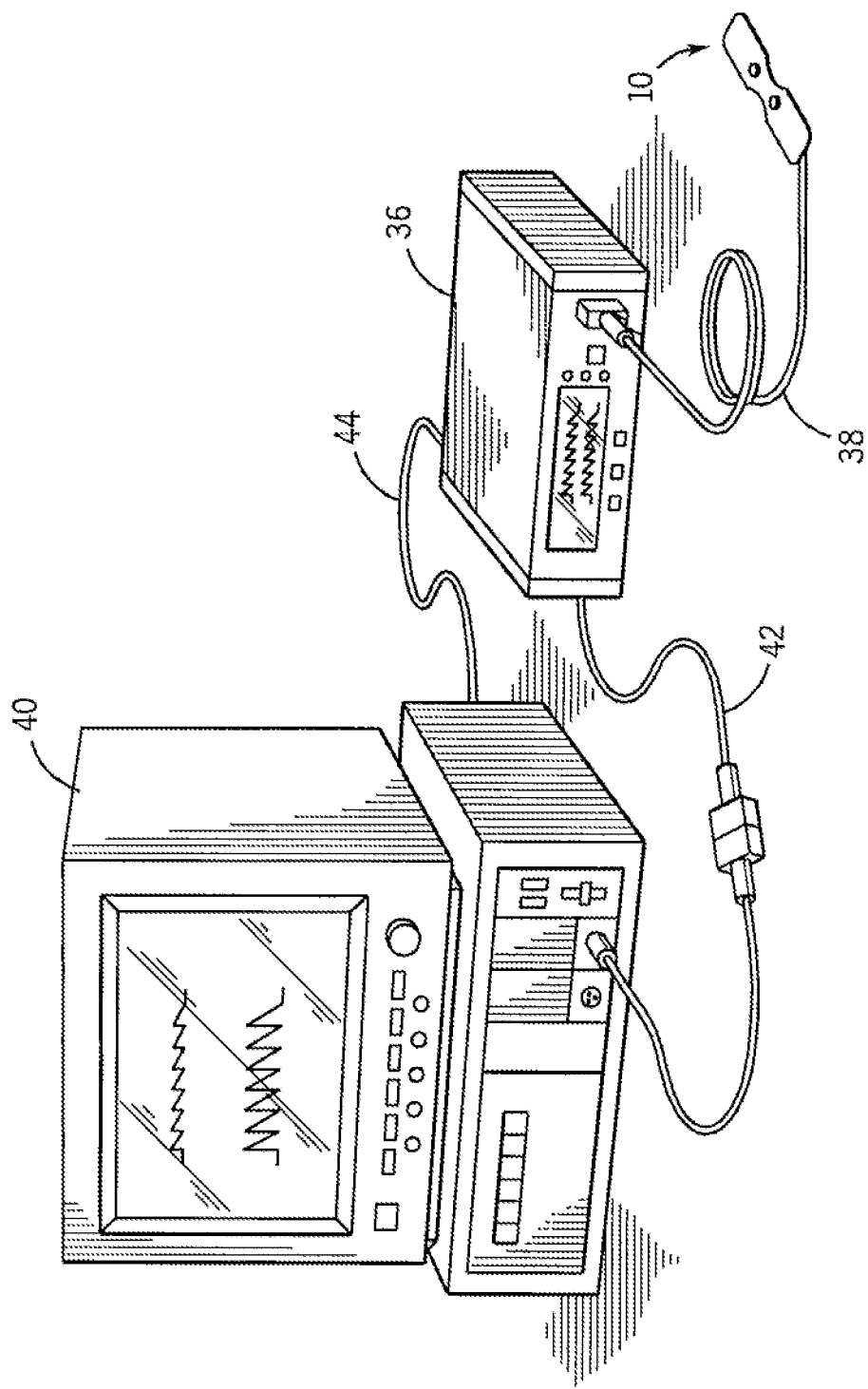
FIG. 12 illustrates a pulse oximetry system coupled to a multi-parameter patient monitor and a sensor according to embodiments of the present invention.

A sensor, illustrated generically as a sensor 10, may be used in conjunction with a pulse oximetry monitor 36, as illustrated in FIG. 12. It should be appreciated that the cable 38 of the sensor 10 may be coupled to the monitor 36 or it may be coupled to a transmission device (not shown) to facilitate wireless transmission between the sensor 10 and the monitor 36. The monitor 36 may be any suitable pulse oximeter, such as those available from Nellcor Puritan Bennett Inc. Furthermore, to upgrade conventional pulse oximetry provided by the monitor 36 to provide additional functions, the monitor 36 may be coupled to a multi-parameter patient monitor 40 via a cable 42 connected to a sensor input port or via a cable 44 connected to a digital communication port.

The sensor 10 includes an emitter 16 and a detector 18 that may be of any suitable type. For example, the emitter 16 may be one or more light emitting diodes adapted to transmit one or more wavelengths of light in the red to infrared range, and the detector 18 may one or more photodetectors selected to receive light in the range or ranges emitted from the emitter 16. Alternatively, an emitter 16 may also be a laser diode or a vertical cavity surface emitting laser (VCSEL). An emitter 16 and detector 18 may also include optical fiber sensing elements. An emitter 16 may include a broadband or "white light" source, in which case the detector could include any of a variety of elements for selecting specific wavelengths, such as reflective or refractive elements or interferometers. These kinds of emitters and/or detectors would typically be coupled to the rigid or rigidified sensor via fiber optics. Alternatively, a sensor 10 may sense light detected from the tissue at a different wavelength from the light emitted into the tissue. Such sensors may be adapted to sense fluorescence, phosphorescence, Raman scattering, Rayleigh scattering and multi-photon events or photoacoustic effects. For pulse oximetry applications using either transmission or reflectance type sensors the oxygen saturation of the patient's arterial blood may be determined using two or more wavelengths of light, most commonly red and near infrared wavelengths. Similarly, in other applications, a tissue water fraction (or other tissue constituent related metric) or a concentration of one or more biochemical components in an aqueous environment may be measured using two or more wavelengths of light. In certain embodiments, these wavelengths may be infrared wavelengths between about 1,000 nm to about 2,500 nm. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present techniques.

The emitter 16 and the detector 18 may be disposed on a sensor body 12, which may be made of any suitable material, such as plastic, foam, woven material, or paper. Alternatively, the emitter 16 and the detector 18 may be remotely located and optically coupled to the sensor 10 using optical fibers. In the depicted embodiments, the sensor 10 is coupled to a cable 38 that is responsible for transmitting electrical and/or optical signals to and from the emitter 16 and detector 18 of the sensor 10. The cable 38 may be permanently coupled to the sensor 10, or it may be removably coupled to the sensor 10—the latter alternative being more useful and cost efficient in situations where the sensor 10 is disposable.

The sensor 10 may be a "transmission type" sensor. Transmission type sensors include an emitter 16 and detector 18 that are typically placed on opposing sides of the sensor site. If the sensor site is a fingertip, for example, the sensor 10 is positioned over the patient's fingertip such that the emitter 16 and detector 18 lie on either side of the patient's nail bed. In other words, the sensor 10 is positioned so that the emitter 16 is located on the patient's fingernail and the detector 18 is located 180° opposite the emitter 16 on the patient's finger pad. During operation, the emitter 16 shines one or more wavelengths of light through the patient's fingertip and the light received by the detector 18 is processed to determine various physiological characteristics of the patient. In each of the embodiments discussed herein, it should be understood that the locations of the emitter 16 and the detector 18 may be exchanged. For example, the detector 18 may be located at the top of the finger and the emitter 16 may be located underneath the finger. In either arrangement, the sensor 10 will perform in substantially the same manner.

Reflectance type sensors also operate by emitting light into the tissue and detecting the light that is transmitted and scattered by the tissue. However, reflectance type sensors include an emitter 16 and detector 18 that are typically placed on the same side of the sensor site. For example, a reflectance type sensor may be placed on a patient's fingertip or foot such that the emitter 16 and detector 18 lie side-by-side. Reflectance type sensors detect light photons that are scattered back to the detector 18. A sensor 10 may also be a "transflectance" sensor, such as a sensor that may subtend a portion of a baby's heel.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of blood oxygen saturation, but these techniques may also be utilized for the measurement and/or analysis of other blood and/or tissue constituents. For example, using the same, different, or additional wavelengths, the present techniques may be utilized for the measurement and/or analysis of carboxyhemoglobin, methemoglobin, total hemoglobin, fractional hemoglobin, intravascular dyes, and/or water content. Rather, the invention is to cover all modifications, equivalents, and alternatives falling within the spirit and scope of the invention as defined by the following appended claims.

What is claimed is:

1. A sensor comprising:
  a conformable bandage-type sensor body configured to be directly applied to a patient's digit;
  an emitter and a detector disposed on the sensor body on a tissue-contacting surface, wherein the emitter and the detector are configured for pulse oximetry measurements; and
  at least one rigid annular structure not fixedly attached to the sensor body and configured to be applied to the sensor body on a surface opposing the tissue-contacting surface with a pressure to retain the sensor body in place on the patient's digit and such that the rigid annular structure covers an area of the sensor body corresponding to the emitter and the detector and covers less than 50% of the surface area of the sensor body when the sensor is applied to the patient.

2. The sensor, as set forth in claim 1, wherein the rigid annular structure comprises a ring.

3. The sensor, as set forth in claim 2, wherein the ring comprises a substantially oval shape.

4. The sensor, as set forth in claim 1, wherein the rigid annular structure comprises an arch, a collar, a thimble or a sleeve.

5. The sensor, as set forth in claim 1, wherein the sensor is configured to operate in reflectance mode.

6. The sensor, as set forth in claim 1, wherein the sensor is configured to operate in transmission mode.

7. The sensor, as set forth in claim 1, wherein the tissue-contacting surface of the sensor body comprises an adhesive layer.

8. The sensor, as set forth in claim 1, wherein the sensor body comprises an alignment index configured to indicate a predetermined position for the rigid annular structure on the sensor body.

9. The sensor, as set forth in claim 1, wherein the rigid annular structure has an adjustable diameter.

10. The sensor, as set forth in claim 1, wherein the rigid annular structure comprises a hinge.

11. The sensor, as set forth in claim 1, wherein the rigid annular structure is configured to cover at least one joint of a patient's digit.

12. The sensor, as set forth in claim 1, wherein the rigid annular structure comprises a foam layer.

13. The sensor, as set forth in claim 1, wherein the rigid annular structure comprises a spring.

14. A physiologic monitoring system comprising:
  a monitor configured to receive a physiological signal; and
  a sensor configured to be operatively coupled to the monitor, the
  sensor comprising:
    a conformable bandage-type sensor body configured to be directly applied to a patient's digit;
    an emitter and a detector disposed on the sensor body on a tissue-contacting surface, wherein the emitter and the detector are configured for pulse oximetry measurements and wherein the detector is configured to provide the physiological signal to the monitor; and
    at least one rigid annular structure not fixedly attached to the sensor body and configured to be applied to the sensor body on a surface opposing the tissue-contacting surface with a pressure to retain the sensor body in place on the patient's digit and such that the rigid annular structure covers an area of the sensor body corresponding to the emitter and the detector and covers less than 50% of the surface area of the sensor body when the sensor is applied to the patient and wherein the rigid annular structure comprises a motion damping structure.

15. The system, as set forth in claim 14, wherein the sensor is coupled to the monitor by a cable.

16. The system, as set forth in claim 14, wherein the motion damping structure comprises a spring.

17. The system, as set forth in claim 14, wherein the motion damping structure comprises a collar.

18. The system, as set forth in claim 14, wherein the motion damping structure comprises a foam layer.

19. A sensor kit comprising:
  a sensor comprising:
    a conformable bandage-type sensor body configured to be directly applied to a patient's tissue;
    at least one sensing element disposed on a tissue-contacting surface of the sensor body; and
  a plurality of rigid annular structures of various sizes adapted to be not fixedly attached to the sensor body and adapted to be applied to the sensor body on a surface opposing the tissue-contacting surface such that, when one of the plurality of rigid annular structures is applied the rigid annular structure covers an area of the sensor body corresponding to the at least one sensing element and covers less than 50% of the surface area of the sensor body when the sensor body is applied to the patient and wherein at least one of the rigid annular structures is configured to apply a pressure to retain the sensor body in place on the patient's tissue.

20. The kit, as set forth in claim 19, wherein the sensor comprises a pulse oximetry sensor.

\* \* \* \* \*